(12) United States Patent
Anand et al.

(10) Patent No.: US 10,675,438 B2
(45) Date of Patent: Jun. 9, 2020

(54) THERAPY SPECIFIC, PRE-PROGRAMMED AUTO INJECTION DEVICE

(71) Applicant: ALCYONE LIFESCIENCES, INC., Lowell, MA (US)

(72) Inventors: PJ Anand, Lowell, MA (US); Deep Arjun Singh, Cambridge, MA (US); Jonathan Freund, Woburn, MA (US); Katelyn Perkins-Neaton, Reading, MA (US); Thomas T. Washburn, Lancaster, MA (US)

(73) Assignee: ALCYONE LIFESCIENCES, INC., Lowell, MA (US)

( * ) Notice: Subject to any disclaimer, the term of this patent is extended or adjusted under 35 U.S.C. 154(b) by 0 days.

(21) Appl. No.: 16/191,275

(22) Filed: Nov. 14, 2018

(65) Prior Publication Data
US 2019/0143038 A1     May 16, 2019

Related U.S. Application Data

(60) Provisional application No. 62/586,498, filed on Nov. 15, 2017.

(51) Int. Cl.
*A61M 25/00* (2006.01)
*A61M 5/172* (2006.01)
(Continued)

(52) U.S. Cl.
CPC .......... *A61M 25/003* (2013.01); *A61M 5/007* (2013.01); *A61M 5/14546* (2013.01);
(Continued)

(58) Field of Classification Search
CPC .............. A61M 5/172; A61M 5/14546; A61M 5/1723; A61M 2205/3331;
(Continued)

(56) References Cited

U.S. PATENT DOCUMENTS

| | | |
|---|---|---|
| 3,623,484 A | 11/1971 | Schulte |
| 4,583,967 A | 4/1986 | Harris |

(Continued)

OTHER PUBLICATIONS

International Application No. PCT/US2018/061380, International Search Report and Written Opinion, dated Feb. 11, 2019.
Office Action, U.S. Appl. No. 16/191,264, dated Feb. 15, 2019.
International Search Report received for PCT/US18/61142 dated Feb. 4, 2019.
Written Opinion received for PCT/US18/61142 dated Feb. 4, 2019.

*Primary Examiner* — Lauren P Farrar
(74) *Attorney, Agent, or Firm* — Marshall, Gerstein & Borun LLP

(57) ABSTRACT

A therapy specific, pre-programmed, hand-held auto-injection device for delivering a drug to a patient includes a housing, a plurality of syringes carried by the housing, at least one actuator disposed within the housing coupled to the plurality of syringes, and a controller disposed within the housing and communicatively coupled to the at least one actuator. The controller is configured to receive an infusion and aspiration profile, which includes an infusion and aspiration protocol for controlling at least one of the plurality of syringes. The controller is also configured to operate the at least one actuator based on the infusion and aspiration protocol by either expelling a fluid from a respective barrel of the plurality of syringes into the infusion and aspiration location or drawing a fluid from the infusion and aspiration location into a respectively barrel of the plurality of syringes.

30 Claims, 15 Drawing Sheets

(51) Int. Cl.
*A61M 5/145* (2006.01)
*A61M 5/00* (2006.01)
*A61M 5/168* (2006.01)
*A61M 25/10* (2013.01)
*A61M 39/02* (2006.01)
*A61M 5/19* (2006.01)
*C12N 15/113* (2010.01)
*C12N 15/11* (2006.01)
*A61M 25/01* (2006.01)
*A61M 25/09* (2006.01)

(52) U.S. Cl.
CPC ............ *A61M 5/168* (2013.01); *A61M 5/172* (2013.01); *A61M 5/1723* (2013.01); *A61M 25/0017* (2013.01); *A61M 25/0032* (2013.01); *A61M 25/0045* (2013.01); *A61M 25/1002* (2013.01); *A61M 25/1011* (2013.01); *A61M 39/0208* (2013.01); *A61M 5/19* (2013.01); *A61M 25/0147* (2013.01); *A61M 25/09* (2013.01); *A61M 2005/1726* (2013.01); *A61M 2025/0007* (2013.01); *A61M 2025/1052* (2013.01); *A61M 2205/0266* (2013.01); *A61M 2205/3303* (2013.01); *A61M 2205/3331* (2013.01); *A61M 2205/3584* (2013.01); *A61M 2205/502* (2013.01); *A61M 2205/52* (2013.01); *A61M 2210/0693* (2013.01); *A61M 2210/1003* (2013.01); *A61M 2230/06* (2013.01); *A61M 2230/42* (2013.01); *C12N 15/111* (2013.01); *C12N 15/113* (2013.01); *C12N 2310/11* (2013.01); *C12N 2320/32* (2013.01); *C12N 2320/35* (2013.01)

(58) Field of Classification Search
CPC .. A61M 2205/3303; A61M 2005/1726; A61M 5/008; A61M 5/19; A61M 5/20; A61M 5/1408
See application file for complete search history.

(56) References Cited

U.S. PATENT DOCUMENTS

| | | |
|---|---|---|
| 4,759,527 A | 7/1988 | Brown |
| 4,795,439 A | 1/1989 | Guest |
| 4,808,157 A | 2/1989 | Coombs |
| 5,468,221 A | 11/1995 | Schoner |
| 5,865,744 A | 2/1999 | Lemelson |
| 2001/0012927 A1 | 8/2001 | Mauch |
| 2002/0049415 A1* | 4/2002 | Fukuda ................ A61M 5/007 604/191 |
| 2004/0075198 A1 | 4/2004 | Schweikert et al. |
| 2004/0243058 A1 | 12/2004 | Barbut et al. |
| 2005/0177097 A1 | 8/2005 | Hildebrand et al. |
| 2006/0079768 A1* | 4/2006 | Small ................ A61M 5/14546 600/432 |
| 2006/0122555 A1 | 6/2006 | Hochman |
| 2006/0173520 A1 | 8/2006 | Olson |
| 2008/0058876 A1 | 3/2008 | Barolat |
| 2008/0103564 A1* | 5/2008 | Burkinshaw ...... A61B 17/00491 607/96 |
| 2008/0200747 A1 | 8/2008 | Wagner et al. |
| 2009/0137926 A1 | 5/2009 | Srinivasan et al. |
| 2011/0054311 A1 | 3/2011 | Williams et al. |
| 2012/0087869 A1 | 4/2012 | Thakker et al. |
| 2012/0245562 A1 | 9/2012 | Bihlmaier |
| 2014/0303238 A1* | 10/2014 | Linsley ................ C07H 21/04 514/44 A |
| 2014/0309590 A1 | 10/2014 | Bahrami et al. |
| 2015/0128873 A1* | 5/2015 | Prescott ............ A61M 5/2066 119/665 |
| 2015/0367071 A1 | 12/2015 | Donnellan et al. |
| 2016/0002627 A1 | 1/2016 | Bennett et al. |
| 2016/0022914 A1 | 1/2016 | Mounce et al. |
| 2016/0369273 A1 | 12/2016 | Freier |
| 2017/0216585 A1 | 8/2017 | Goldfarb et al. |
| 2018/0028761 A1 | 2/2018 | Anand et al. |

* cited by examiner

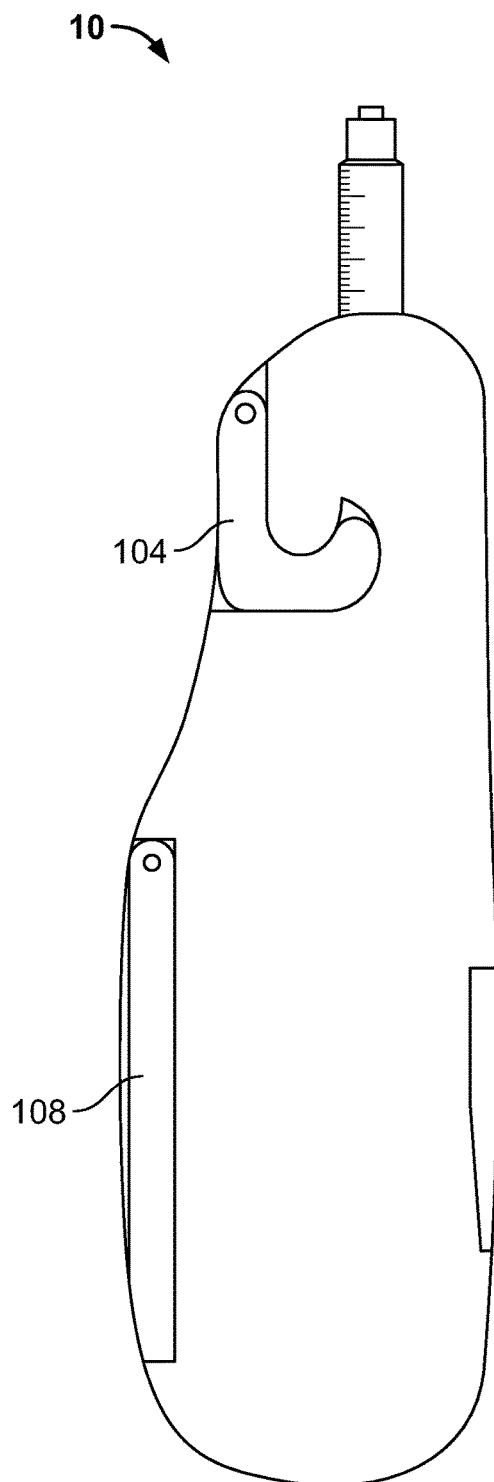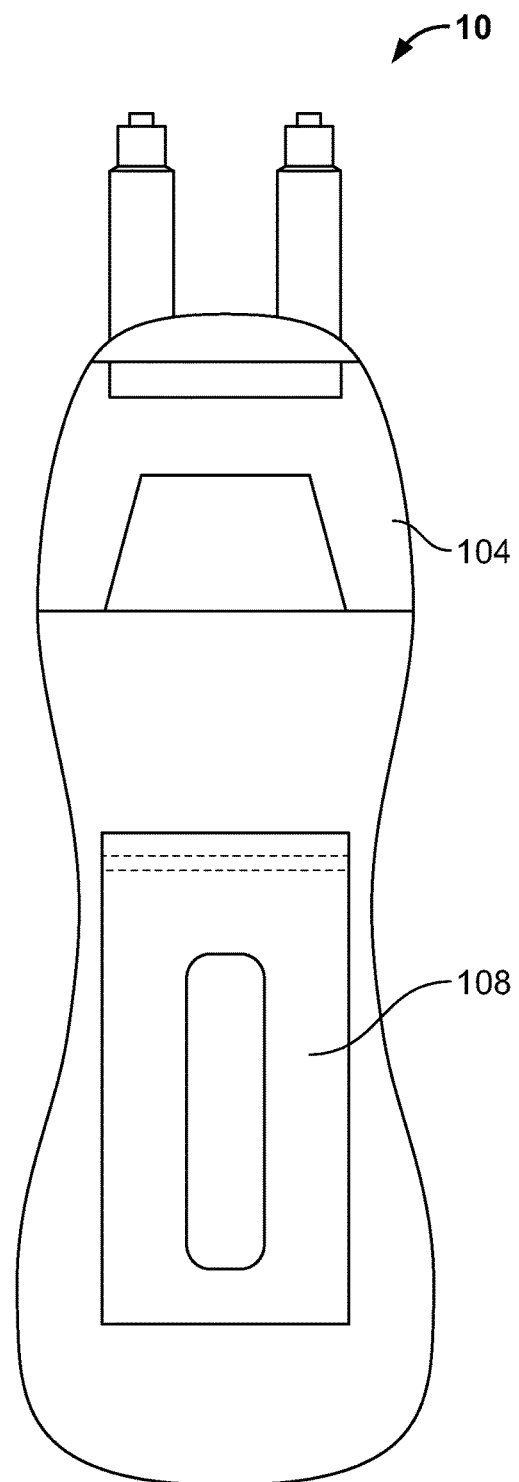
FIG. 15  FIG. 16

THERAPY SPECIFIC, PRE-PROGRAMMED AUTO INJECTION DEVICE

CROSS-REFERENCE TO RELATED APPLICATIONS

This application claims priority benefit of U.S. Provisional Application No. 62/586,498, entitled "Intrathecal Delivery Devices and Methods" and filed Nov. 15, 2017, the disclosure of which is incorporated by reference in its entirety.

FIELD OF THE DISCLOSURE

The present disclosure generally relates to an auto-injection device and, more particularly, to an auto-injection device for facilitating injection of a fluid into a patient based on a therapy specific, pre-programmed infusion and aspiration profile.

BACKGROUND

Many systems of the human body depend upon careful regulation of fluid pressure, volume, flow, and metabolite balance. For example, the intrathecal space is the fluid-filled compartment below the arachnoid mater of the spinal cord. Fluctuations in intrathecal pressure can result in, e.g., reduced local tissue blood flow, reduced metabolite delivery to the spinal cord, and increased intracranial pressure. Delivery of fluids to the intrathecal space is challenging, as a needle (optionally associated with a catheter) is manually inserted into the spine of a patient. Other dangers associated with intrathecal drug administration include infusing a drug too quickly or introducing too much fluid into the space, resulting in a pressure build-up leading to dangerous complications. These considerations are not unique to the intrathecal administration; controlled delivery of material to fluid compartments at other anatomical sites (e.g., an intracerebroventricular site, an intratumoral site) is desired. The training and time required to manually adapt existing drug delivery devices to different anatomical sites and specific treatments represents a significant burden to clinicians.

SUMMARY

In accordance with a first exemplary aspect of the present disclosure a therapy specific, pre-programmed, hand-held auto-injection device for delivering a drug to a patient is disclosed. The hand-held auto-injection device includes a housing, a plurality of syringes carried by the housing and adapted to be fluidly coupled to an infusion and aspiration location in a patient, at least one actuator disposed within the housing, and a controller disposed within the housing and communicatively coupled to the at least one actuator. Each of the plurality of syringes includes a barrel partially disposed within the housing, a plunger rod movably disposed within the barrel, and a stopper disposed at a proximal end of the plunger rod and disposed within the barrel. At least one of the plurality of syringes includes a fluid. The at least one actuator includes a plurality of shafts coupled to a distal end of a respective plunger rod such that the actuator controls the position of each plunger rod. Each plunger rod may be moved by the actuator between a first position, in which each stopper is spaced from a proximal end of a respective barrel, and a second position, in which each stopper sealingly engages the proximal end of the respective barrel. The controller is configured to retrieve an infusion and aspiration profile from a memory of the controller. The infusion and aspiration profile includes an infusion and aspiration protocol for at least one of the plurality of syringes. The controller is configured to operate the at least one actuator based on the infusion and aspiration protocol, which involves moving the plurality of shafts to change the position of the plurality of plunger rods. Movement of the plunger rods from the first position to the second position expels fluid from a respective barrel and into the infusion and aspiration location, and movement of the plunger rods from the second position to the first position draws fluid from the infusion and aspiration location into the respective barrel.

In accordance with a second exemplary aspect of the present disclosure a therapy specific, pre-programmed, hand-held auto-injection device for delivering a drug to a patient is disclosed. The hand-held auto-injection device includes a housing, a plurality of syringes carried by the housing and adapted to be fluidly coupled to an infusion and aspiration location in a patient, at least one actuator disposed within the housing, at least one sensor disposed in the hang-held device and configured to monitor a pressure associated with the patient, and a controller disposed within the housing and communicatively coupled to the at least one actuator. Each of the plurality of syringes includes a barrel partially disposed within the housing, a plunger rod movably disposed within the barrel, and a stopper disposed at a proximal end of the plunger rod and disposed within the barrel. At least one of the plurality of syringes includes a fluid. The at least one actuator includes a plurality of shafts coupled to a distal end of a respective plunger rod such that the actuator controls the position of each plunger rod. Each plunger rod may be moved by the actuator between a first position, in which each stopper is spaced from a proximal end of a respective barrel, and a second position, in which each stopper sealingly engages the proximal end of the respective barrel. The controller is configured to receive an infusion and aspiration profile, which includes an infusion and aspiration protocol for at least one of the plurality of syringes. The controller is configured to operate the at least one actuator based in part on the infusion and aspiration protocol and the monitored pressure, which involves moving the plurality of shafts to change the position of the plurality of plunger rods. In particular, movement of the plunger rods from the first position to the second position expels the fluid from a respective barrel and into the infusion and aspiration location, and movement of the plunger rods from the second position to the first position draws fluid from the infusion and aspiration location into the respective barrel.

In further accordance with the foregoing first and/or second aspects, the fluid contained within at least one of the plurality of syringes may include, for example, an antisense oligonucleotide that targets mRNA encoding Huntington protein (HTT) or an antisense oligonucleotide that targets mRNA encoding survival motor neuron-2 (SMN2).

BRIEF DESCRIPTION OF THE DRAWINGS

The features of this disclosure which are believed to be novel are set forth with particularity in the appended claims. The present disclosure may be best understood by reference to the following description taken in conjunction with the accompanying drawings, in which like reference numerals identify like elements in the several figures, in which:

FIG. 15 is a side view of the auto-injection device of FIG. 2, but including an example mounting device.

FIG. 16 is a rear view of the auto-injection device of FIG. 15.

DETAILED DESCRIPTION

The present disclosure is generally directed to an auto-injection device for facilitating injection of a fluid into a patient and/or aspiration of a fluid from the patient. The auto-injection device disclosed herein substantially mitigates the risks associated with delivering therapeutic agents intrathecally (e.g., injecting or removing fluid too rapidly, creating a risky fluid pressure at the point of injection or removal, leakage of cerebrospinal fluid, catheter fracture, kink, migration, or releases of large concentrations of therapeutic agents, etc.). The auto-injection device substantially mitigates those risks by delivering or removing fluid based on a therapy specific, pre-programmed infusion and aspiration profile, and monitors at least one physiological parameter and pressure associated with the patient.

Figure 1:
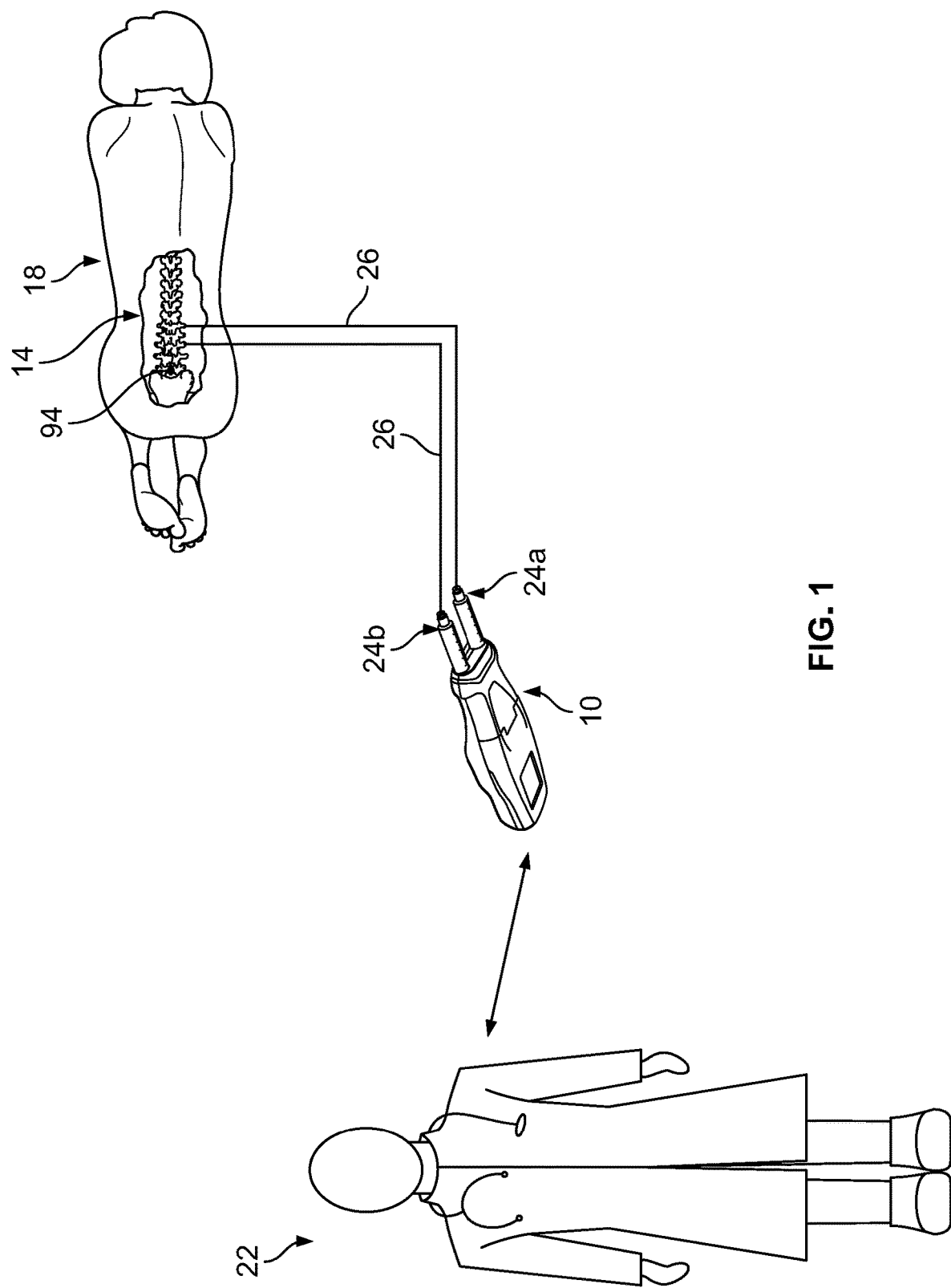
FIG. 1 illustrates an example of an auto-injection device constructed in accordance with the teachings of the present disclosure and positioned in the vicinity of an infusion and aspiration location of a patient by a clinician.
Figure 2:
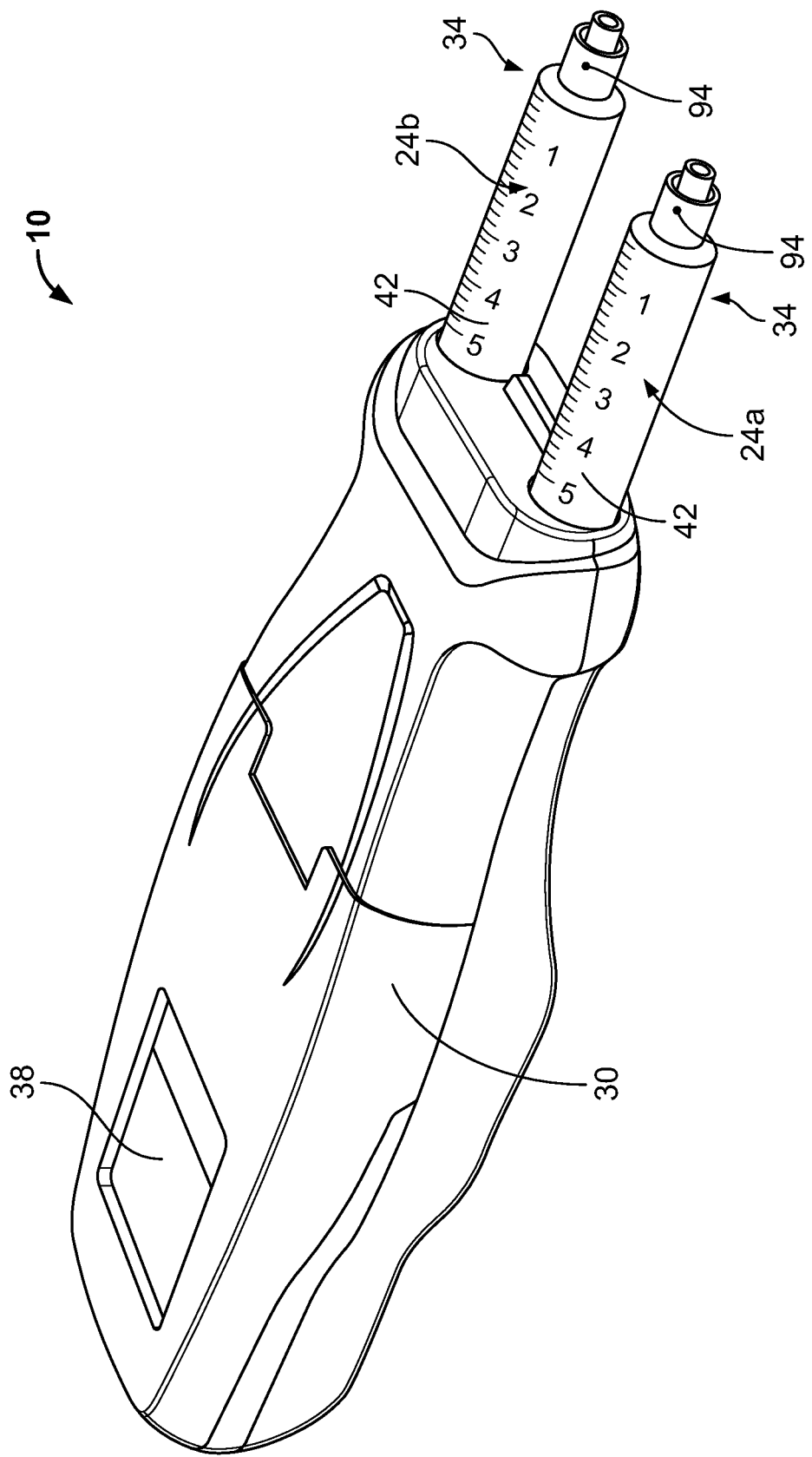
FIG. 2 is a perspective view of the auto-injection device of FIG. 1.
Figure 3:
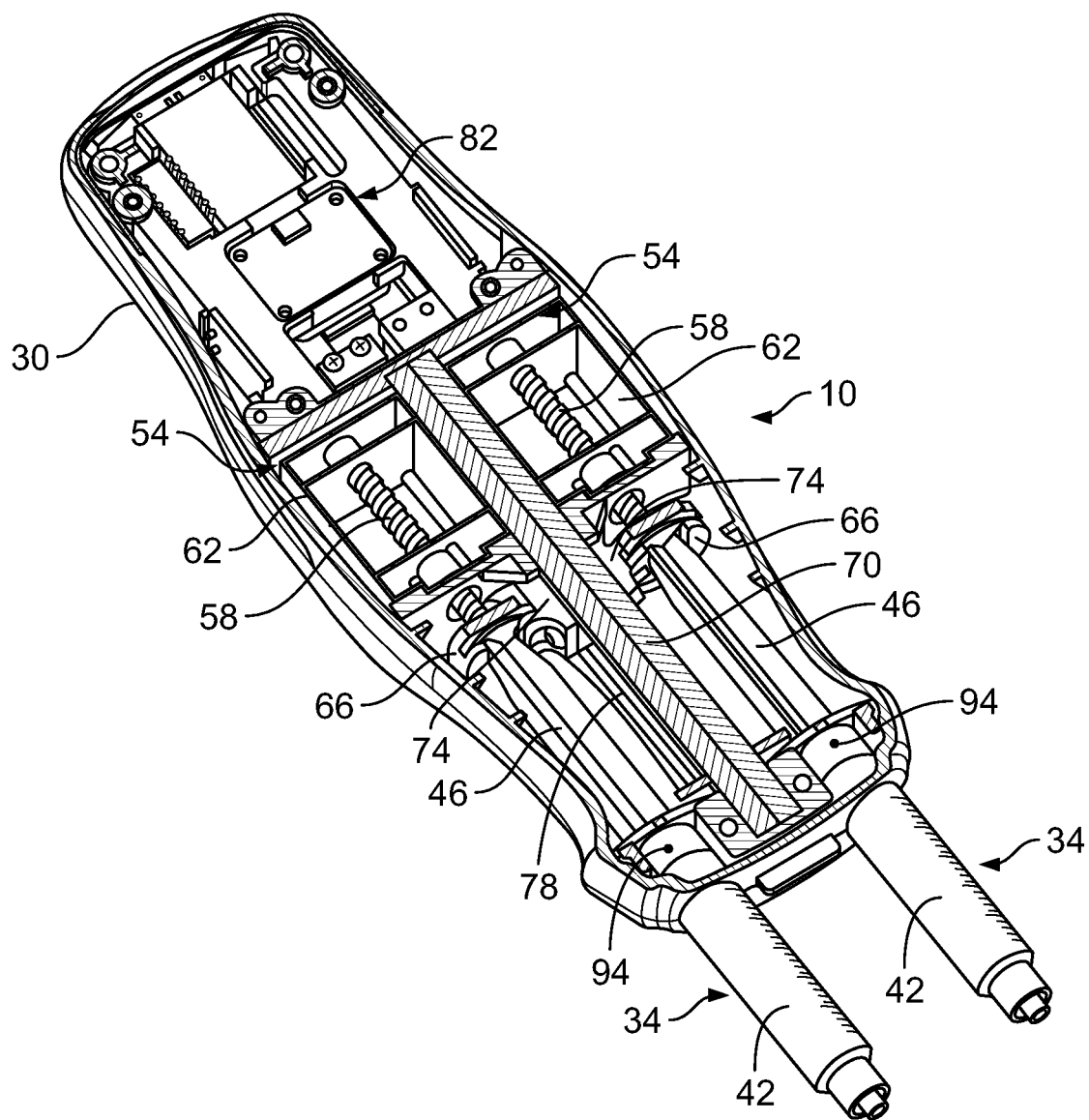
FIG. 3 is a perspective, cut-away view of the auto-injection device of FIG. 2.
Figure 4:
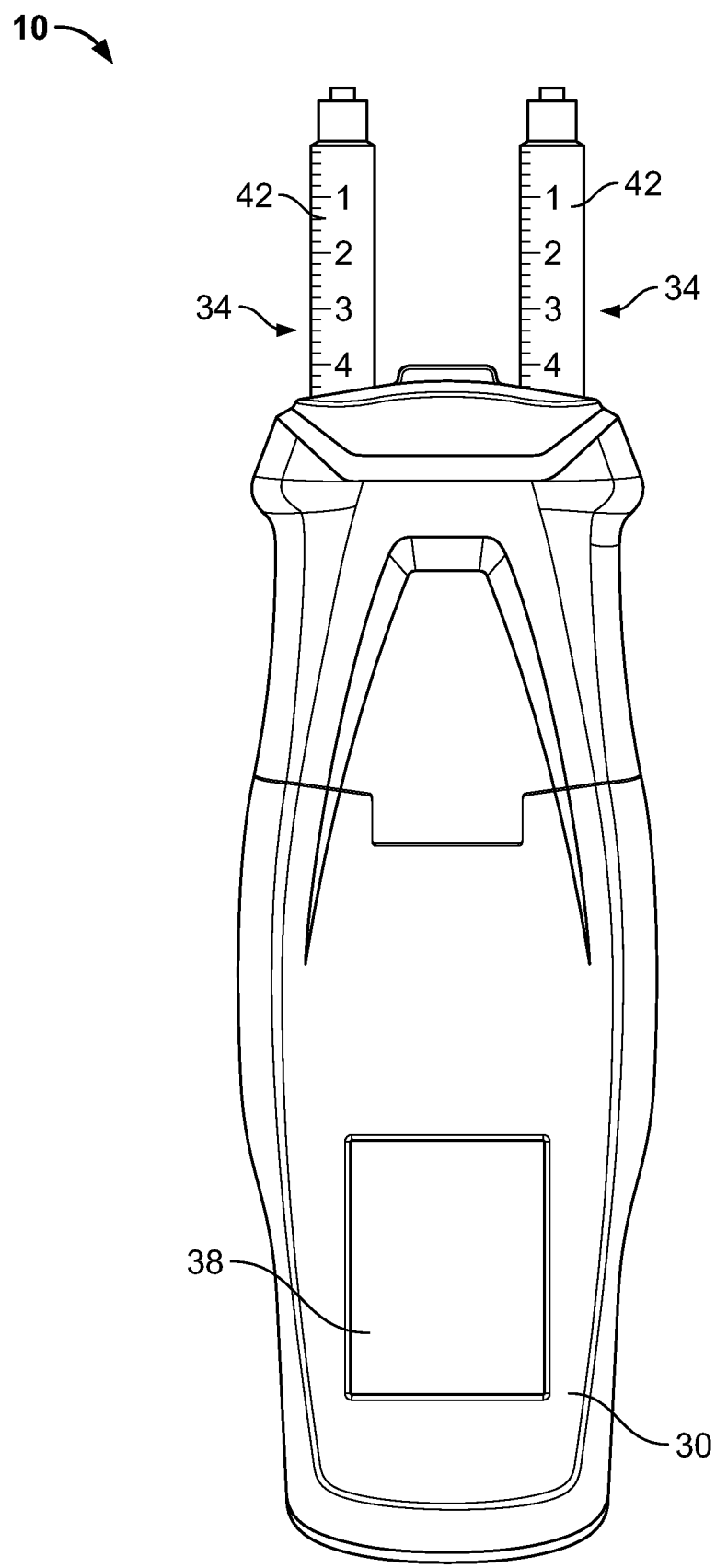
FIG. 4 is a top view of the auto-injection device of FIG. 2.

FIG. 1 illustrates an example of an auto-injection device 10 constructed in accordance with the teachings of the present disclosure and positioned in proximity to an infusion and aspiration location 14 of a patient 18 by a clinician 22. The infusion and aspiration location 14 may, for example, be an intrathecal location (e.g., the intrathecal space), an intracerebroventricular location, or an intratumoral location. The clinician 22 may use the device 10 to, for example, deliver a fluid (e.g., a therapeutic agent) 24a to the infusion and aspiration location 14 of the patient 18 and/or remove fluid 24b (e.g., cerebrospinal fluid) from the infusion and aspiration location 14 of the patient 18. In such an example, the device 10 contains the fluid 24a and delivers the fluid 24a to the infusion and aspiration location 14 and/or removes the fluid 24b from the infusion and aspiration location 14 through a catheter 26 fluidly coupled to the device 10 and the infusion and aspiration location 14. Once the device 10 is fluidly coupled to the infusion and aspiration location 14 via the catheter 26, the clinician 22 may activate the device 10 to begin delivery of the fluid 24a (i.e., infusion) to the infusion and aspiration location 14 and/or removal of the fluid 24b (i.e., aspiration) from the infusion and aspiration location 14. In particular, once activated, the device 10 delivers the fluid 24a to and/or removes the fluid 24b from the infusion and aspiration location 14 based on a pre-programmed infusion and aspiration profile. It will be appreciated that the device 10 may be pre-programmed with the infusion and aspiration profile off-site, e.g., by someone other than the clinician 22, or on-site, e.g., by the clinician 22 prior to using the device 10 on the patient 18. As an example, the clinician 22 may enter an infusion and aspiration profile that includes, for example, a volume and a flow rate of the infusion and/or aspiration necessary for the patient 18. In some cases, the device 10 may be pre-programmed, off-site, with the infusion and aspiration profile and then modified by the clinician 22 and/or modified responsive to at least one pressure and/or at least one physiological parameter associated with the patient 18. It will be appreciated that in some examples, the device 10 can be constructed to be MR capable (i.e., so the device 10 does not interfere with imaging techniques such as magnetic resonance imaging, etc.)

FIGS. 2-9 will now be used to discuss further details regarding the auto-injection device 10. The device 10 in this example generally includes a housing 30, a plurality of syringes 34 carried by (e.g., partially disposed within) the housing 30 and adapted to be fluidly coupled to the infusion and aspiration location 14, and a display 38 disposed on the housing 30. In this example, the housing 30 has a substantially rectangular shape that is ergonomic and allows the housing 30 to be hand-held. In particular, a majority of the weight of the device 10 may be concentrated toward a proximal end of the housing 30, which allows the device 10 to sit comfortably within the palm of the clinician 22 or the patient 18. In this example, the plurality of syringes 34 is disposed at a distal end of the housing 30 and the display 38 is disposed at a proximal end of the housing 30. However, in other examples, the display 38 can be disposed at the distal end and the plurality of syringes 34 can be disposed at the proximal end. The display 38 may be a touch screen that facilitates interaction with the patient 18 and the clinician 22 through a user interface ("UI"). In particular, the UI may display the operational status of the device 10 (e.g., on, off, infusing, aspirating, infusing and aspirating) as well as receive input from the patient 18 and/or the clinician 22. The UI may, for example, allow the clinician 22 to start, stop, pause, or continue operation of the device 10. The UI may also allow the clinician 22 to pre-program the device 10 prior to use of the device 10 as well as receive other input from the clinician 22, such as, for example, modifications to the infusion and aspiration profile during operation of the device 10. Additionally, the UI may display various physiological parameters and pressures monitored by the device 10.

As best depicted in FIGS. 4-8, the plurality of syringes 34 in this example includes two syringes 34 carried by the housing 30 and partially disposed within the housing 30. In other examples, however, the plurality of syringes 34 may include more than two syringes 34 (e.g., four syringes 34). In any case, each one of the plurality of syringes 34 includes a barrel 42 partially disposed within the housing 30 and adapted to hold the fluid 24a and/or receive the fluid 24b (depending on how the device 10 is to be used), a plunger rod 46 movably disposed within the barrel 42, and a stopper 50 disposed at a proximal end of the plunger rod 46 and disposed within the barrel 42. Coupled to the plurality of syringes 34 is at least one actuator 54 that is disposed within the housing 30. In this example, one actuator 54 is coupled to each of the plurality of syringes 34, such that two actuators 54 are employed. However, in other examples, more or less actuators 54 may be employed. Each of the at least one actuators 54 include a shaft 58 coupled to a proximal end of a respective one of the plunger rods 46 and a driver 62 that is connected to the shaft 58 and controls the position of the respective plunger rod 46 via the shaft 58. Thus, the device 10 includes a first driver 62 that is connected to a first shaft 58 that is in turn coupled to a first plunger rod 46 of a first syringe 34, and a second driver 62 that is connected to a second shaft 58 that is in turn coupled to a second plunger rod 46 of a second syringe 34. In particular, the drivers 62 control the position of the plunger rods 46 and, in turn, the flow of fluid to and/or from the infusion and aspiration location 14, by translating the shafts 58 toward a proximal end of the respective barrel 42 or away from the proximal end of the respective barrel 42. In some examples, the driver(s) 62 may translate the shaft(s) 58 at a constant rate, while in other examples, the driver(s) 62 may translate the shaft(s) 58 by pulsating the linear movement of the shaft(s) 58 or in a stepwise manner. In some examples, the driver(s) 62 may translate the shaft(s) 58 according to various pre-programmed modes such as, for example, a bolus mode, a variable flow rate mode, a target volume mode, a target time mode, a sync mode (where the cycles could be synced to sensor input data), or the like. Initially, the plunger rod 46 may be in a first position, wherein the stopper 50 is spaced a maximum distance away from the proximal end of the barrel 42, a second position, wherein the stopper 50 sealingly engages the proximal end of the barrel 42, or an intermediate position, wherein the stopper 50 is between the first position and the second positions.

The actuator(s) 54 and plurality of syringes 34 of the device 10 may have any of the following specifications: a driver operational accuracy of ±0.25%; a flow accuracy of the driver of ±2%; reproducibility of ±0.05%; syringe compatibility of 250 μl to 50 ml; a minimum flow rate of 1 μl/min; a maximum flow rate of 100 ml/min; and adjustable linear force up to 75 lbs.; a minimum plunger travel rate of about 0.24 mm/min (assuming a scale length of 250 μl syringe=60 mm and 50 ml syringe=81 mm); a maximum plunger travel rate of about 51 mm/min (assuming a scale length of 250 μl syringe=60 mm and 50 ml syringe=81 mm); a standard AC/DC adapter; and capability to detect two independent stalls. The driver could, in some examples, include a 0.9 degree stepper motor control (equivalent to 400 step/rev) or a 1.8 degree stepper motor control (equivalent to 200 step/rev), and a microprocessor with 1/32 microstepping or 1/16 microstepping.

The plurality of syringes 34 may house a variety of fluids 24a within the barrel 42. For example, the fluid 24a may comprise a therapeutic agent such as a nucleic acid, a protein therapeutic, a cell therapy, a small molecule, a viral vector encoding a therapeutic protein, or a combination thereof.

Examples of protein therapeutics include antibody-based therapeutics, such as antibodies, antibody fragments, or antibody-like protein products that include binding regions of antibodies (e.g., scFv, diabodies, antibody mimetics, and the like). The antibody-based therapeutic may target, e.g., amyloid plaques, tau proteins, cancer antigens, or abnormal alpha-synuclein. Examples of protein therapeutics also include, but are not limited to, hormones, enzymes (e.g., lysosomal enzymes, such as alpha-L-iduronidase, N-acetyl-galactosamine-4-sulfatase, or beta-glucuronidase), growth factors (e.g., fibroblast growth factor (FGF) or neurotrophins or neurotrophic factors, such as glial cell-derived neurotrophic factor (GDNF), brain-derived neurotrophic factor (BDNF), ciliary neurotrophic factor (CNTF), or nerve growth factor (NGF)), blood factors, bone morphogenetic proteins, interferons, interleukins, and thrombolytics. Examples of cell-based therapies include, but are not limited to, stem cell therapeutics and immune cells (including modified immune cells, such as CAR T cells). Suitable small molecule therapeutics include, but are not limited to, analgesics, ion channel blockers, anti-convulsive agents, antibiotics or antiviral agents, anti-inflammatories, anticoagulants, chemotherapeutic, anti-depressants, anti-anxiety agents, steroids, and the like. In various aspects, the therapeutic agent is baclofen, morphine, bupivacaine hydrochloride, clonidine hydrochloride, gabapentin, idursulfase, cytarabine, methotrexate, a corticosteroid, edavarone-conjugate, conotoxin, abomorphine, prednisolone hemisuccinate sodium, carbidopa/levodopa, tetrabenazine, benzodiazepines, such as diazepam and midazolam, alphaxalone or other derivative, cyclophosphamide, idursulfase (Elaprase®), iduronidase (Aldurazyme®), topotecan, buslfan, opmaveloxolone, epicatechin, methylprednisolone, frataxin replacement, reservatrol, nicontinamide, AT-010 (RNA that induces splicing modulation in the mature amyloid precursor protein mRNA), Cerebril™, an anti-Aβ antibody, elenbecestat, a corticosteroid, or nusinersen (Spinraza®), or combinations thereof.

Nucleic acid therapeutics include DNA or RNA, which may be single stranded or double stranded and which may be modified or unmodified. In particular, the nucleic acid may be an antisense oligonucleotide, a ribozyme, an miRNA, an siRNA, and shRNA, or a nucleic acid encoding a clustered regularly interspaced short palindromic repeats ("CRISPR") associated protein (Cas) system, or combination thereof. The CRISPR/Cas system is further described in, e.g., U.S. Patent Publication Nos. 2018/0223311.

Optionally, the nucleic acid targets a gene (or gene product, such as mRNA) selected from the group consisting of APP, MAPT, SOD1, BACE1, CASP3, TGM2, TARDBP, ADRB1, CAMK2A, CBLN1, CDK5R1, GABRA1, MAPK10, NOS1, NPTX2, NRGN, NTS, PDCD2, PDE4D, PENK, SYT1, TTR, FUS, LRDD, CYBA, ATF3, CASP2, HRK, C1QBP, BNIP3, MAPK8, MAPK14, Rac1, GSK3B, P2RX7, TRPM2, PARG, CD38, STEAP4, BMP2, GJA1, TYROBP, CTGF, ANXA2, DUOX1, RTP801, RTP801L, NOX4, NOX1, NOX2 (gp91pho, CYBB), NOX5, DUOX2, NOXO1, NOXO2 (p47phox, NCF1), NOXA1, NOXA2 (p67phox, NCF2), p53 (TP53), HTRA2, KEAP1, SHC1, ZNHIT1, LGALS3, SESN2, SOX9, ASPP1, CTSD, CAPNS1, FAS, FASLG, CAPN1, FADD, CASP1, CASP9, p75NTR, PARK2, HTT (with expanded repeats), NogoA, MAG, OMGP, NgR1, PDE4, BCAN, NCAN, PTPRZ1, TNC, NRP1, NRP2, PLXNA1, PLXNA2, PLXNB1, PLXNC1, TROY, LRRC1, ROCK1, LimK1, LimK2, CFL1, KCNC4, KCNE3, NAT8L, FKBP1A, FKBP4, LRRK2, DYRK1A, AKAP13, UBE2K, WDR33, MYCBP2, SEPHS1, HMGB1, HMGB2, TRPM7, BECN1, THEM4, SLC4A7, MMP9, SLC11A2, ATXN3, ATXN1, ATXN7, PRNP, EFNB3, EPHA4, EFNA5, EPHA7 and EFNB2, such that gene expression or function is modified.

In some embodiments, the therapeutic agent is an oligonucleotide comprising at least one modified nucleotide, optionally a modified nucleotide that reduces binding to cerebral spinal fluid (CSF) proteins. In various embodiments, the modified nucleotide includes a substituent at the 2'-position, such as a 2'-O-2-methoxyethyl ("2'-MOE") group, as shown below, wherein X is O or S.

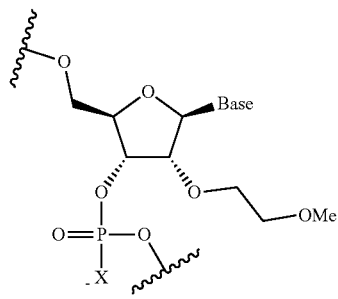

Oligonucleotides comprising a 2'-MOE modification can distribute rapidly in central nervous system tissues. Oligonucleotides comprising such modifications exhibit extended half-lives in CSF and central nervous system tissues, which can result in less frequent dose administration.

In some cases, the modified nucleotide can include a 2',4'-constrained group, such as a constrained 2'-O-ethyl ("cEt") group. In various cases, the cEt group can have S-stereochemistry ("S-cEt"), as shown below, wherein X is O or S.

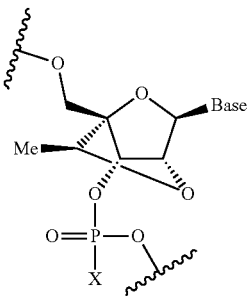

Nucleic acids modified with a constrained ethyl group, such as S-cEt, can exhibit enhanced thermal stability, good potency, and a good therapeutic profile.

In various embodiments, the nucleic acid is an antisense nucleic acid reduces expression of HTT (e.g., HTT with expanded repeats). The sequence of HTT is known, see, e.g., GenBank Accession No. NM_002111. In some embodiments, the nucleic acid is an antisense nucleic acid that targets mRNA encoding Huntington protein (HTT), such as mutant HTT (e.g., HTT with expanded repeats). In various aspects, the nucleic acid comprises the nucleic acid sequence ctcagtaacattgacaccac. In various aspects, the nucleic acid is used in connection with the device in a method of treating Huntington's disease.

In various aspects, the nucleic acid is a modified antisense oligonucleotide that targets survival motor neuron-2 (SMN2) mRNA, optionally the intron downstream of exon 7 of the SMN2 transcript. The sequence of SMN2 is known, see, e.g., GenBank Accession No. NM_022876. Optionally, the antisense oligonucleotide is modified such that the 2'-hydroxy groups of the ribofuranosyl rings are replaced with 2'-O-2-methoxyethyl groups and the phosphate linkages are replaced with phosphorothioate linkages. In various aspects, the nucleic acid is nusinersen and is used in connection with the device in a method of treating spinal muscular atrophy (SMA).

Optionally, the nucleic acid encodes a beneficial protein that, e.g., replaces an absent or defective protein, or encodes a cytotoxic protein that achieves a therapeutic effect, such as cancer cell death. Any of the protein-based therapeutics described herein may be delivered to a subject via delivery of a nucleic acid encoding the protein under conditions which allow expression in vivo. For example, in various embodiments, the nucleic acid encodes a neurotrophic factor such as, but not limited to, nerve growth factor (NGF), brain-derived neurotrophic factor (BDNF), neurotrophin-3 (NT-3), neurotrophin-4/5 (NT-4/5), neurotrophin-6 (NT-6), ciliary neurotrophic factor (CNTF), glial cell line-derived neurotrophic factor (GDNF), the fibroblast growth factor family (e.g., FGF's 1-15), leukemia inhibitory factor (LIF), certain members of the insulin-like growth factor family (e.g., IGF-1), a neurturin, persephin, a bone morphogenic protein (BMPs), an immunophilin, a member of the transforming growth factor (TGF) family of growth factors, a neuregulin, epidermal growth factor (EGF), platelet-derived growth factor (PDGF), vascular endothelial growth factor family (e.g. VEGF 165), follistatin, or Hifl, or combinations thereof.

Optionally, the fluid comprises a gene expression (e.g., viral) vector. Examples of viral vectors include, e.g., herpes simplex virus (HSV) vectors, adenovirus (Ad) vectors, parvoviral-based vectors (e.g., adeno-associated viral vectors), chimeric Ad-AAV vectors, and retroviral vectors (including lentiviral vectors, HIV vectors). In some embodiments, the viral vector is an AAV vector.

Alternatively, the fluid 24a disposed within the barrel 42 may be a diagnostic agent. The fluid 24a may be a contrast media such as imaging agent or radiocontrast agent. In particular, the contrast media may be iohexol, iodixanol, ioversol, or barium sulfate.

In any case, when one or more of the barrels 42 includes the fluid 24a, movement of the plunger rod(s) 46 from the first position to the second position, or from the first position to the intermediate position, expels the fluid 24a from the barrel(s) 42 and into the infusion and aspiration location 14. Movement of the plunger rod(s) 46 from the first position to the second position or from the first position to the intermediate position may, for example, expel 0.1 to 1.0 mL of the fluid 24a into the infusion and aspiration location 14. Conversely, movement of the plunger rod(s) 46 from the second position to the first position, or from the second position to the intermediate position, draws the fluid 24b into the barrel(s) 42 from the infusion and aspiration location 14. Movement of the plunger rod(s) 46 from the second position to the first position or from the second position to the intermediate position may, for example, aspirate 0.1 to 1.0 mL of the fluid 24b into the barrel(s) 42. In some examples, the actuator 54 moves the plunger rod 46 of a first syringe 34 and then, once the plunger rod 46 of the first syringe 34 moves to the desired position, the actuator 54 moves the plunger rod 46 of a second syringe 34 to the desired position. In other examples, the actuator 54 moves the plunger rod 46 of the second syringe 34 to the desired position once the plunger rod 46 of the first syringe 34 is in the process of moving to the desired position. In yet other examples, the actuators 54 may simultaneously move the respective plunger rods 46 of the plurality of syringes 34. In such an example, the actuators 54 can move the respective plunger rods 46 in the same direction (e.g., move the plunger rods 46 from the first position to the second position) or in opposite directions (e.g., move a first plunger rod 46 from the first position to the second position and move a second plunger rod 46 from the second position to the first position).

Figure 5:
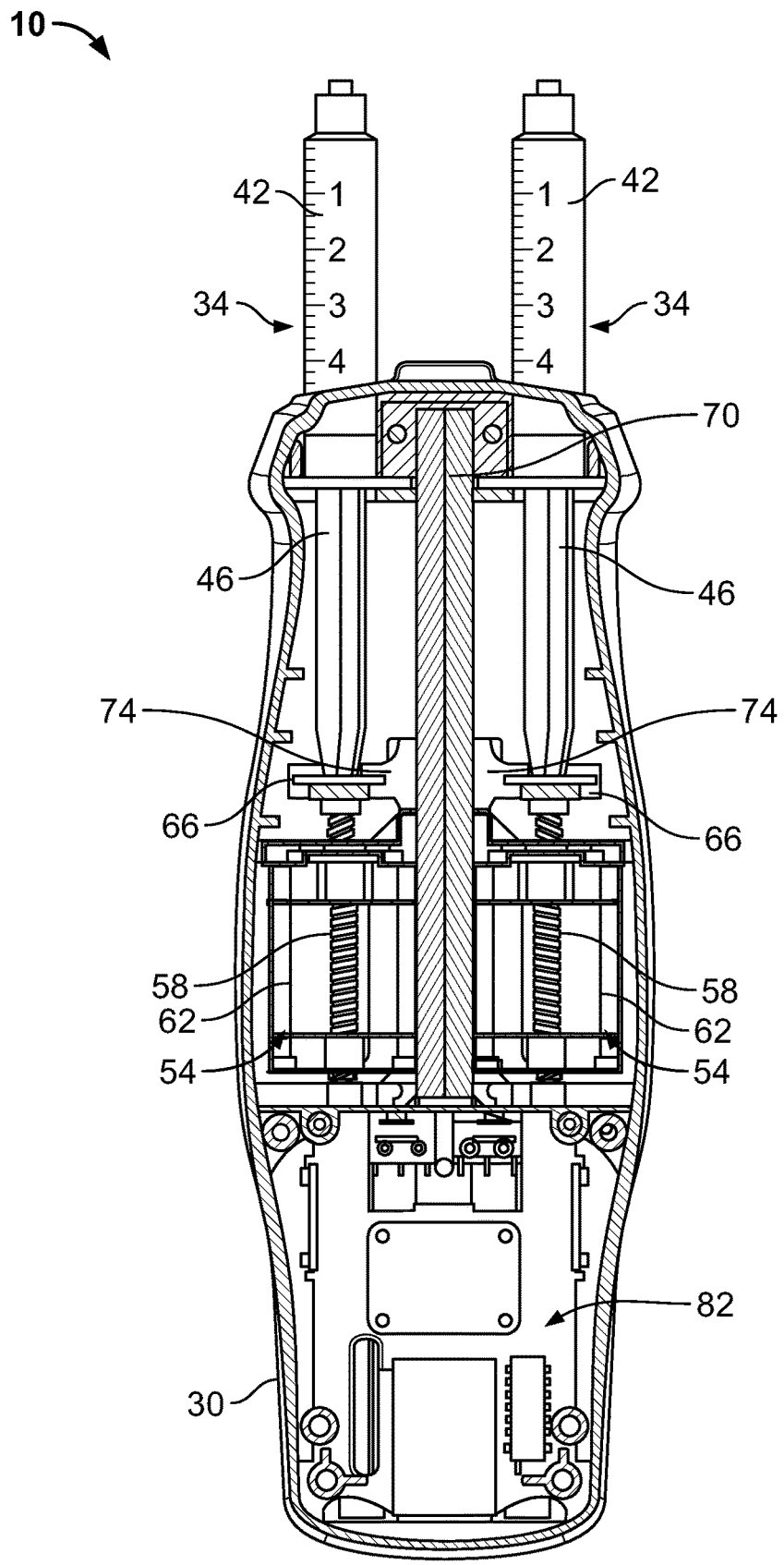
FIG. 5 is a top view of the auto-injection device of FIG. 4, but with a top portion of the device removed.
Figure 6:
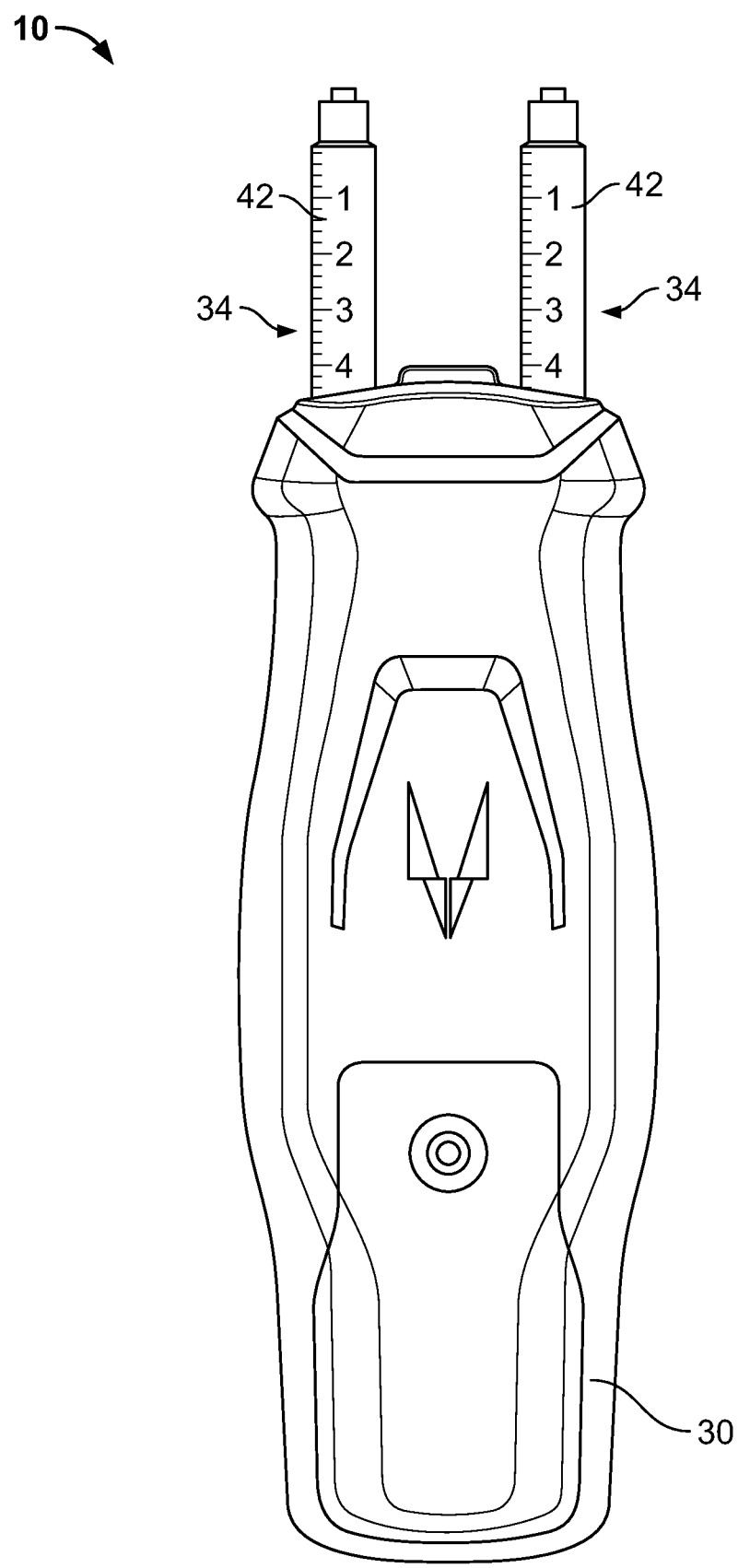
FIG. 6 is a bottom view of the auto-injection device of FIG. 2.
Figure 7:
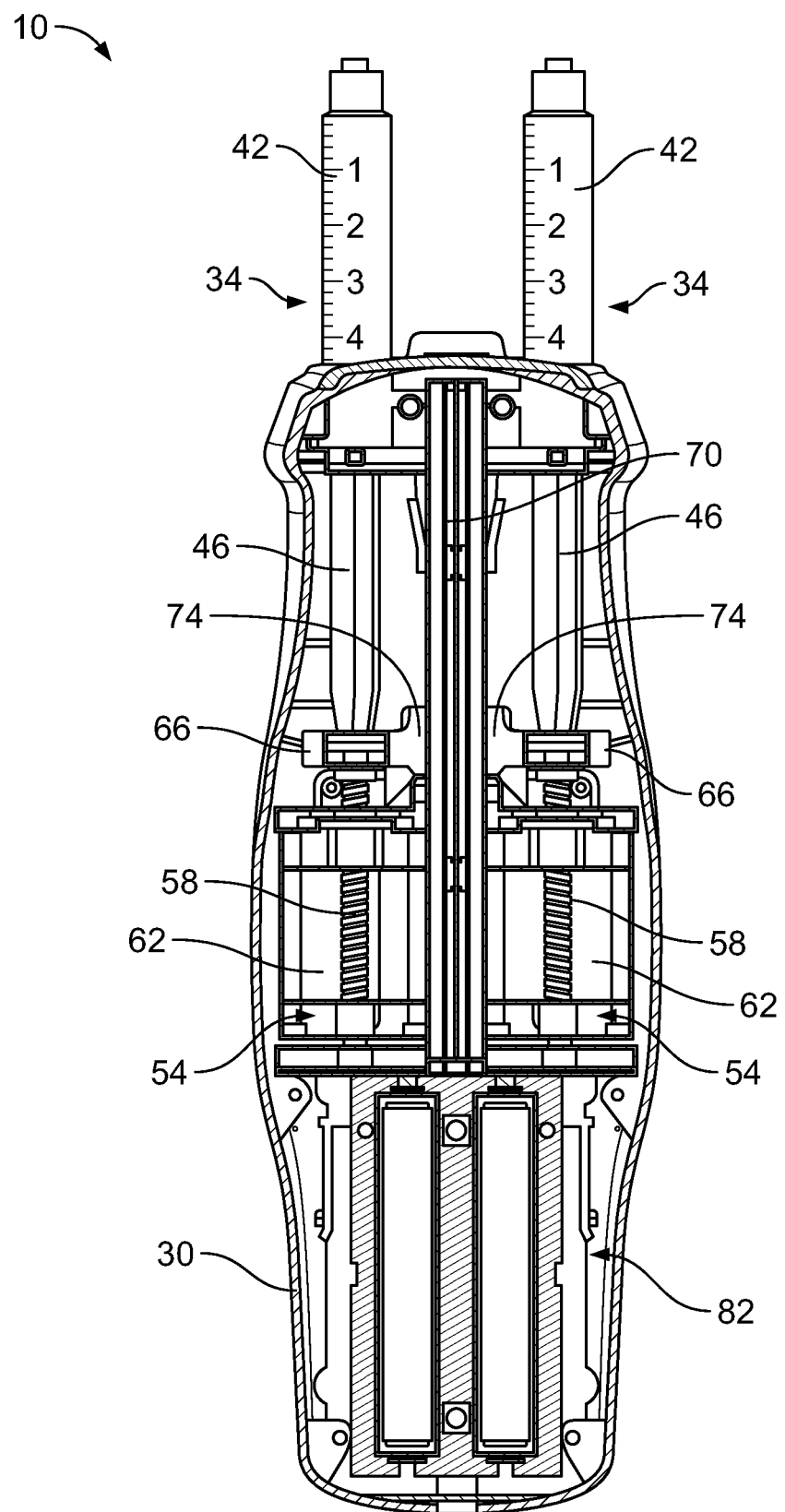
FIG. 7 is a bottom view of the auto-injection device of FIG. 6, but with a bottom portion of the device removed.
Figure 8:
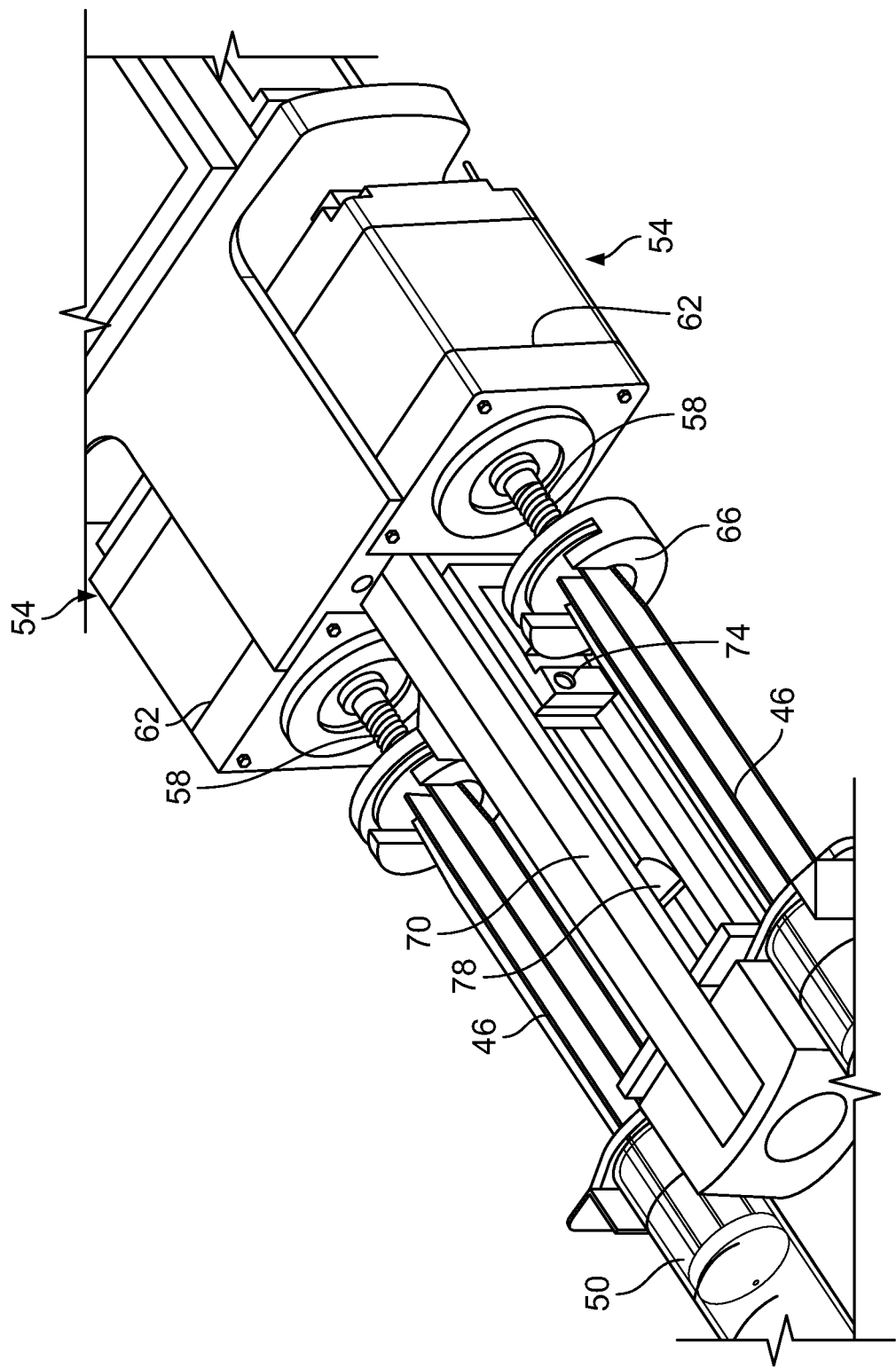
FIG. 8 is a detailed view of a first portion of the auto-injection device of FIG. 2, but with the housing removed for clarity.
Figure 9:
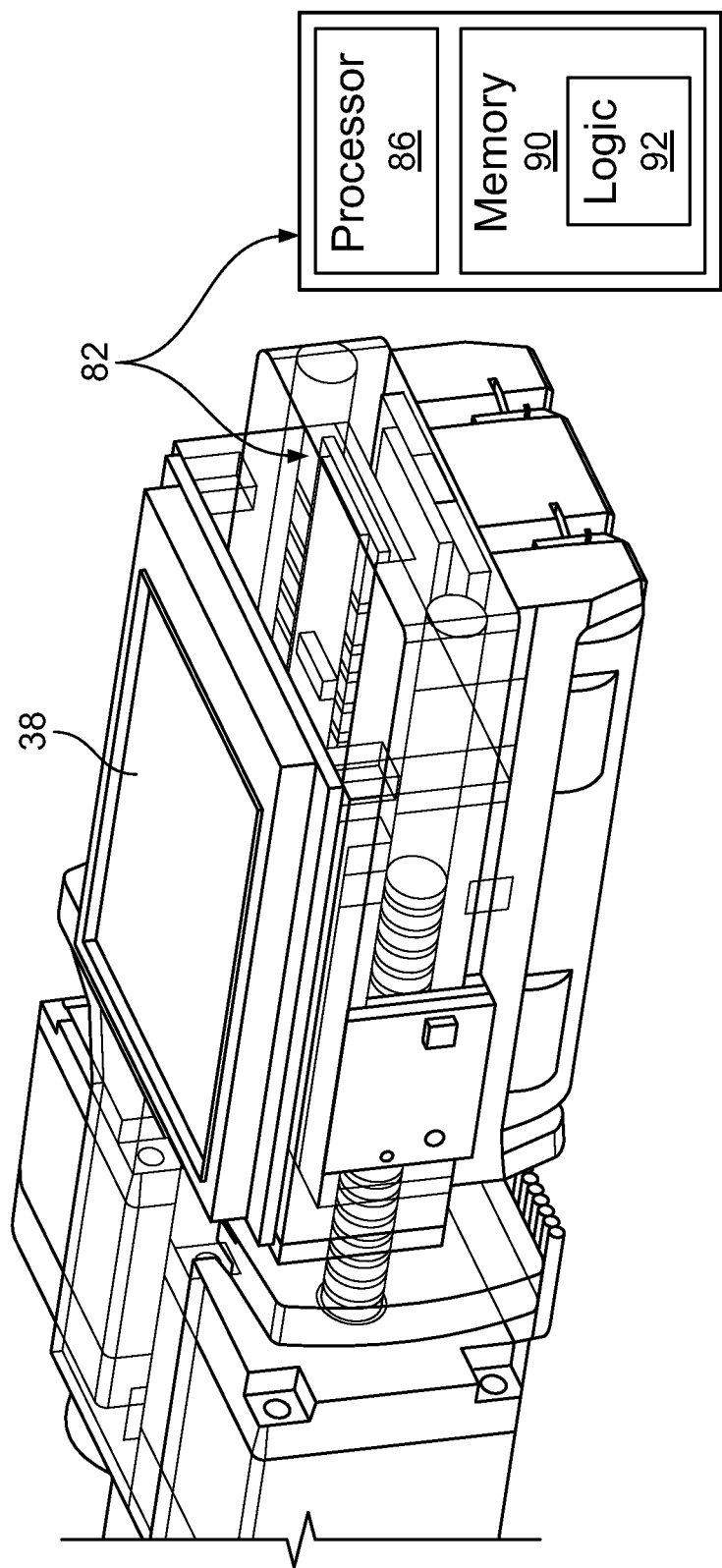
FIG. 9 is a detailed view of a second portion of the auto-injection device of FIG. 2, but with the housing removed for clarity.
Figure 10:
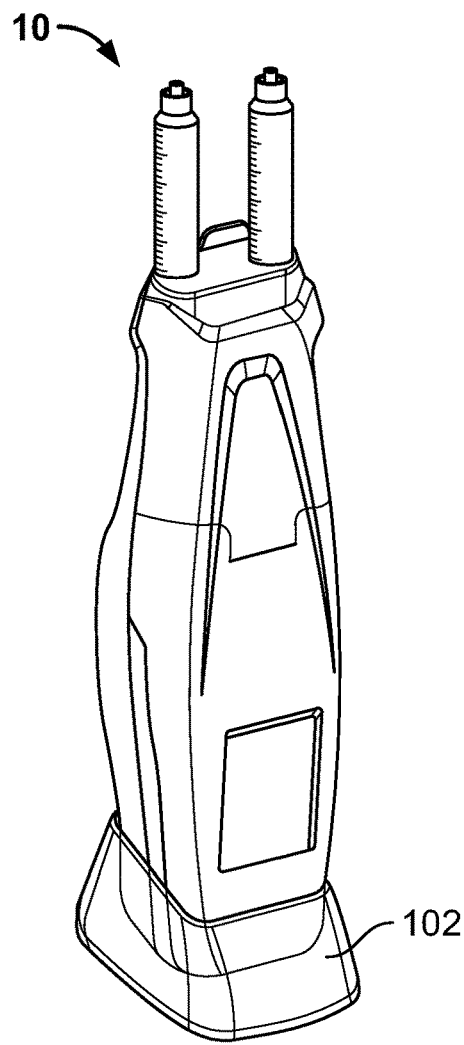
FIG. 10 is a perspective view of the auto-injection device of FIG. 2, but mounted on one example of a stand.
Figure 11:
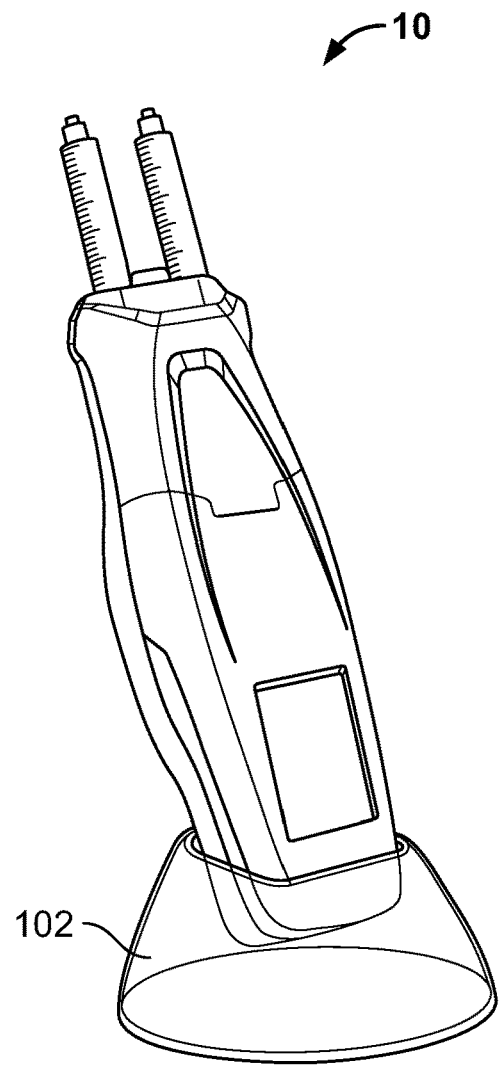
FIG. 11 is a perspective view of the auto-injection device of FIG. 2, but mounted on another example of a stand.

Each shaft 58 of the device 10 may be any shaft 58 that allows for smooth linear translation. In particular, the shaft 58 may, for example, be a metal shaft, a carbon fiber shaft, or a shaft made from a light weight polymer. As discussed above, each shaft 58 is coupled to the proximal end of the respective plunger rod 46. In this example, the shafts 58 are releasably coupled to the plunger rod 46 of the respective syringe 34 via a coupling 66, as depicted in FIGS. 5, 7, and 8, such that a portion of the housing 30 can be opened and the syringe 34 can be decoupled from the coupling 66 (and, in turn, the shaft 58) and removed from the housing 30. As best depicted in FIG. 8, the proximal end of the plunger rods 46 takes the shape of a "T" in cross section, and the couplings 66 are disposed at a distal end of a respective shaft 58 to slidably receive the "T" shaped portion of the proximal end of the plunger rod 46. Each coupling 66 may include an opening that slidably receives the proximal end of the respective plunger rod 46 and secures that plunger rod 46 to the respective shaft 58. The plunger rods 46 may be removably or fixedly coupled to the shafts 58, respectively, in a variety of other ways. For example, each plunger rod 46 can threadingly engage a respective shaft 58.

The device 10 may also include a partition 70 disposed within the housing 30 that separates a first syringe 34 and a first actuator 54 from a second syringe 34 and a second actuator 54. The partition 70 may also include a groove 74 that receives a guide 78 that is attached to the respective couplings 66. In some examples, the guide 78 and the coupling 66 are integrally formed and, in other examples, the guide 78 and coupling 66 are releasably attached to one another. In any event, the partition 70, the groove 74, and the guide 78 assist in the linear translation of the shafts 58 and plunger rods 46 between the first, second, and intermediate positions. In particular, the groove 74 and the guide 78 ensure that the shafts 58 and plunger rods 46 follow a linear path as the shafts 58 and the plunger rods 46 move between the first, second, and intermediate positions. Such a feature limits the possibility that the plunger rod(s) 46 translate(s) at an angle, thereby dislodging the syringe(s) 34 from the device 10 or causing the syringe(s) 34 to disconnect from the catheter 26. Additionally, the partition 70 physically separates the barrels 42 from one another such that, for example, the outlets of the plurality of syringes 34 (where fluid is expelled into or drawn from the infusion and aspiration location 14) are spaced apart.

As discussed above, the drivers 62 are coupled to the shafts 58, respectively, and control the position of the respective plunger rods 46 via the shafts 58 and, thus, the flow of fluid out of or into the barrels 42, respectively. Each driver 62 may be any driver that can linearly translate the shaft 58. For example, the drivers 62 may be linear actuators, pneumatic actuators, electro-magnetic actuators, spring loaded actuators, etc. In other examples, the driver 62 can be a pneumatic rotary actuator. In such an example, the shafts 58 could be a linear screw that, as the drivers 62 rotate, linearly translate to move the plunger rods 46, respectively, between the first, intermediate, and second positions.

The device 10 also includes a controller 82 disposed in the housing 30. The controller 82 is communicatively coupled to the actuators 54 and controls the position of actuators 54, which ultimately controls the movement of the shafts 58 and the plunger rods 46 to infuse the fluid 24a into the infusion and aspiration location 14 and/or aspirate the fluid 24b from the infusion and aspiration location 14. The controller 82 includes a processor 86 that implements an infusion and aspiration profile stored in a memory 90 of the controller 82. The infusion and aspiration profile stored in the memory 90 includes an infusion and aspiration protocol for at least one of the syringes 34. Generally speaking, the processor 86 communicates with the actuators 54 to execute the infusion and aspiration protocol. For example, the controller 82 can be communicatively coupled to the actuators 54 using a hardwired communication scheme which may include the use of any desired hardware, software and/or firmware to implement hardwired communications, including, for example, standard 4-20 mA communications, and/or any communications using any smart communication protocol such as the FOUNDATION® Fieldbus communication protocol, the HART® communication protocol, RS-485, RS-232, etc.

The processor 86 may be a general processor, a digital signal processor, ASIC, field programmable gate array, graphics processing unit, analog circuit, digital circuit, or any other known or later developed processor. The processor 86 operates pursuant to the infusion and aspiration profile stored in the memory 90. The memory 90 may be a volatile memory or a non-volatile memory. The memory 90 may include one or more of a read-only memory ("ROM"), random-access memory ("RAM"), a flash memory, an electronic erasable program read-only memory ("EEPROM"), or other type of memory. The memory 90 may include an optical, magnetic (hard drive), or any other form of data storage.

The infusion and aspiration protocol, which is part of the infusion and aspiration profile stored on the memory 90, is a set of executable instructions that controls at least one of the syringes 34 to facilitate infusion and/or aspiration of the fluid 24a, 24b into the patient 18 using the device 10. The infusion and aspiration protocol may be stored on the memory 90 as computing logic 92, which includes one or more infusion and aspiration routines and/or sub-routines, embodied as computer-readable instructions stored on the memory 90. The controller 82, particularly the processor 86 thereof, can execute the logic 92 to cause the processor 86 to retrieve the infusion and aspiration profile and control the actuators 54 in accordance with the infusion and aspiration profile in order to facilitate the desired infusion and/or aspiration of the fluid 24a, 24b into the patient 18. In particular, the infusion and aspiration protocol may specify, among other parameters, whether each of the syringes 34 is to infuse the fluid 24a into the infusion and aspiration location 14 or aspirate the fluid 24b from the infusion and aspiration location 14, the timing of infusion and/or aspiration (i.e., when the plunger rods 46 are to be moved), a volume of the fluid 24a to be infused into the infusion and aspiration location 14 from the barrel(s) 42, the flow rate for infusing the fluid 24a into the infusion and aspiration location 14 from the barrel(s) 42, a volume of the fluid 24b to be aspirated from the infusion and aspiration location 14 into the barrel(s) 42, the flow rate for aspirating the fluid 24b from the infusion and aspiration location 14 into the barrel(s) 42.

Additionally, other data, such as at least one physiological parameter and at least one pressure associated with the patient 18, may be stored in the memory 90. The at least one physiological parameter and the at least one pressure may be previously obtained values (e.g., values measured during a previous use of the device 10, values input into the UI via the clinician 22, values received via a wired or wireless communication protocol) or values measured during the use of the device 10, either directly by the device 10 or by another device associated with the device 10 and received using a wired or wireless communication protocol. In particular, the at least one physiological parameter may include parameters associated with the infusion and aspiration location 14 or other parameters for the patient 18, such as, for example, a cerebrospinal fluid pressure, a cerebrospinal flow rate, an intratumoral pressure, a cerebroventricular pressure, a heart rate, a respiration rate, a protein level, a biomarker presence, absence, or level, respiration per minute ("RPM"), respiratory diaphragm movements, electrical inputs for patient electrocardiography, or combinations thereof. The at least one pressure may include, for example, an in-line pressure, an infusion pressure, an aspiration pressure, arterial/venous pressure, force limits for different syringe types, other pressure values, or combinations thereof. Additionally, the other data may include various functional variables such as, for example, fluid volumes, number of infusion and aspiration cycles, and time delay between cycles.

The device 10 may also be associated with one or more sensors that measure one or more of these parameters. In some cases, the device 10 may include at least one sensor 94 disposed in the housing 30 that measures one or more of these parameters. In one example, the device 10 may include a pressure sensor 94 that measures the in-line pressure. Alternatively or additionally, at least one sensor 94 may be disposed in the infusion and aspiration location 14 that measures one or more of these parameters. The one or more sensors 94 in turn electronically communicate with the controller 82 using any known electronic communication methods. For example, the controller 82 may be communicatively connected to the one or more sensors 94 using a hardwired communication scheme as described in detail above, using one or more known wireless communication protocols, or a combination thereof. In particular, communication between the controller 82 and the sensors 94 may be facilitated using the WirelessHART® protocol, the Ember protocol, a WiFi protocol, and IEEE wireless standard, etc. A protocol stack operation may be used by these communication protocols to receive, decode, route, encode and send wireless signals via an antenna to implement wireless communications between the controller 82 and the sensors 94.

In some other examples, the device 10 may be communicatively coupled to at least one sensor 94 disposed on or in the patient 18 at a location other than the infusion and aspiration location 14. In some examples, the at least one sensor 94 may be disposed in various locations on the body of the patient 18 to measure various physiological parameters. For example, the at least one sensor 94 could include a body position sensor, which detects changes in the position of the patient 18, a temperature sensor, which detects the overall temperature of the patient 18 or the temperature of a specific part of the body of the patient 18, an electromyography ("EMG") sensor, which measures muscle response or electrical activity of the patient 18, an electrocardiogram ("ECG" or "EKG") sensor, which measures the electrical activity of the heart of the patient 18, an airflow sensor, a galvanic skin response ("GSR") sensor, which measures the electrical conductance of the skin of the patient 18, or combinations thereof. While these sensors have been discussed as being placed on the patient 18, the at least one sensor 94 may also be placed in an article of clothing (e.g., a vest, etc.) worn by the patient 18. In such an example, the article of clothing (e.g., a vest, etc.) could inflate to exert a compressive force against the body of the patient 18 and deflate to decompress the force exerted against the body of the patient 18. The compression and decompression may be timed to coincide with infusion and/or aspiration, which may assist in the diffusion of the fluid 24a within the infusion and aspiration location 14.

Moreover, the device 10 may provide various alarms based on issues detected by the at least one sensor 94. In particular, the device 10 may issue an alarm when the at least one sensor 94 detects that the measured physiological parameter or pressure is greater than a threshold physiological parameter or pressure. The alarm could be, for example, an audible, tactile, or visual alarm issued by the device 10.

In some cases, the infusion and aspiration profile may be stored on a memory outside of the device 10 and transmitted to the device 10 prior to usage of the device 10. For example, the infusion and aspiration profile can be stored on a memory of a desktop computer which communicates with the device 10 wirelessly or through a hardwired connection using any of the wireless communication or hardwired communication protocols discussed above. In other examples, the infusion and aspiration profile can be stored on a memory of a mobile electronic device, a smart phone, or a server located away from the device 10. Additionally, the infusion and aspiration profile may be stored on an external memory and transferred to the memory 90 of the device 10 through a hardwired connection. For example, the infusion and aspiration profile can be stored on an external hard drive, a solid-state drive ("SSD"), a portable digital storage device, the Cloud, a Personal Cloud, or a USB Flash Drive, and then transferred to the memory 90. The device 10 may also be communicatively coupled to an external computing device that could, for example, compare the measured at least one physiological parameter and/or at least one pressure to a threshold physiological parameter and/or pressure to determine if the measured at least one physiological parameter and/or at least one pressure is within an acceptable, threshold range. For example, the external computing device could be a desktop computer, a tablet, a mobile phone, server, etc.

The device 10 may be communicatively coupled to additional devices or systems located externally from the device 10. For example, the device 10 may be communicatively coupled to a remote control. In such an example, the remote control could be used instead of or in conjunction with the display to turn the device 10 on and off, pause and stop infusion and/or aspiration, select the infusion and aspiration profile, etc. As another example, the device 10 could be communicatively coupled to a visual guide that emits light and instructs the patient to perform an action (e.g., breathe, etc.) in connection with the operation of the device 10. In such an example, the light emitting device may be a single light emitting diode ("LED") capable of emitting various colors (e.g., white, blue, red, green, yellow, etc.) and emitting various patterns of light (e.g., strobe, flash, flicker, pulse, etc.). The color as well as the pattern of the light emitted may be used to apprise the patient 18 and/or clinician 22 of various alerts or to instruct the patient 18 and/or clinician 22 to perform an action.

Additionally, the device 10 may include an extension line 100 that extends through the housing 30 and is coupled to the catheter 26. In such an example, various endoscopic instruments may be inserted through the extension line 100 and catheter 26 in order to access the infusion and aspiration location 14. For example, a spinal needle could be inserted through the extension line 100. In other examples, various sensors such as those discussed above could be inserted through the extension line 100. Further, a peristaltic pump may be fluidly coupled to the extension line and may recirculate fluid as part of the infusion and aspiration protocol.

Further, the device 10 may include a clamping system (not shown) that seals tubing (e.g., catheters, cannulas, lumens, etc.) at pre-programmed times. In particular, the clamping system may include a carrier tube partially disposed within the housing 30 and a clamping mechanism disposed within the housing 30. In some examples, the carrier tube could be the extension line 100. The clamping mechanism could include, in some examples, an actuator having a driver coupled to a shaft and a clamp axially disposed on the carrier tube and coupled to the shaft. The driver causes the shaft to translate linearly, which, in turn, causes the clamp to engage and seal the carrier tube. The carrier tube slidably receives the tubing through a port and could be fluidly coupled to the plurality of syringes 34. As mentioned above, in some examples, the clamping system could seal the tubing at pre-programmed times. In such an example, the controller 82 transmits a signal to the actuator, which causes the driver to linearly translate the shaft in a first direction placing the clamp into engagement with the carrier tube and sealing the carrier tube and tubing carried by the carrier tube restricting fluid flow therethrough. Additionally, the controller 82 could transmit a signal to the actuator causing the driver to linearly translate the shaft in a second direction removing the clamp from engagement with the carrier tube and opening the carrier tube and tubing carried by the carried tube permitting fluid flow therethrough.

In some examples, the clamping system could be disposed outside of the housing 30, proximate to the plurality of syringes 34. In such an example, the clamping mechanism could be attached to the tubing that is coupled to each of the plurality of syringes 34, thereby restricting or permitting flow through the tubing as discussed above. Such a clamping mechanism reduces the possibility of forming air embolisms, exsanguination (blood loss), and contamination.

Moreover, the device 10 may include an automated priming system, which detects and eliminates air disposed within any of the fluid lines (e.g., catheters coupled to each of the plurality of syringes 34, extension lines, etc.) of the device 10. The automated priming system, in some examples, could include a sensor (e.g., one of the sensors 94) disposed within the tubing configured to detect air, priming vials containing priming fluid and disposed within the housing 30, a pump disposed within the housing 30 to draw the priming fluid from the priming vials and push the priming fluid through the fluid lines until there is no longer air disposed within the fluid lines, or combinations thereof.

Figure 12:
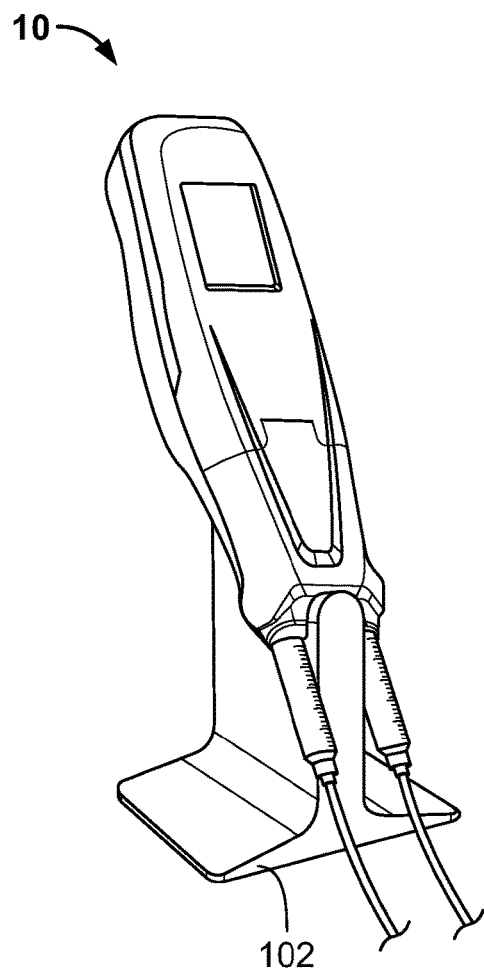
FIG. 12 is a perspective view of the auto-injection device of FIG. 2, but mounted on yet another example of a stand.
Figure 13:
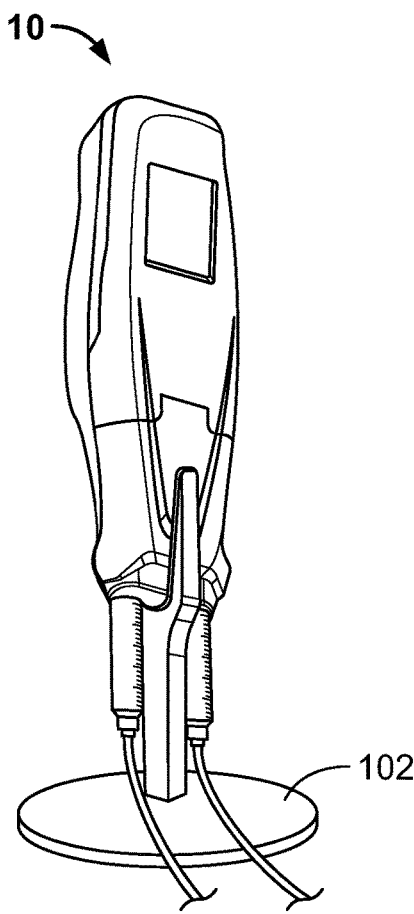
FIG. 13 is a perspective view of the auto-injection device of FIG. 2, but mounted on yet another example of a stand.
Figure 14:
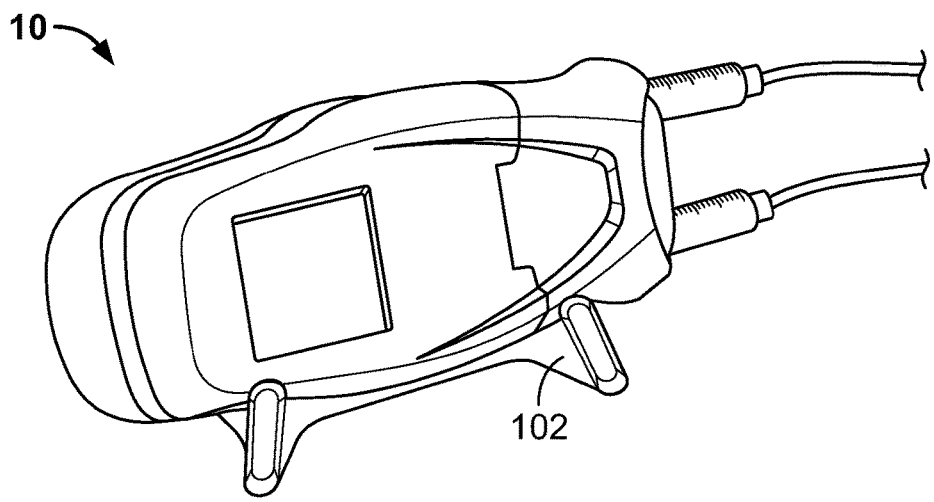
FIG. 14 is a perspective view of the auto-injection device of FIG. 2, but mounted on yet another example stand.

Optionally, the device 10 may also be equipped with one or more accessories to facilitate storage, transportation, and/or positioning of the device 10. The device 10 may, for example, be equipped with a stand 102, as depicted in FIGS. 10-14. The stands 102 depicted in FIGS. 10-13 carry and hold the device in a stable, substantially upright position. Such stands 102 may include a swivel feature which improves visibility of the display 38 and could self-orient if the catheters 26 are repositioned. The stands 102 depicted in FIGS. 10-12, orient the device 10 at an angle, which increases visibility of the display 38 and the plurality of syringes 34. However, in such an example, to prevent the device 10 from tipping over because it is on an angle, the stand 102 could include a larger footprint to counteract the shift in the center of mass of the device 10. The stands 102 depicted in FIGS. 12 and 13 provide the additional benefits of orienting the display 38 in a position better for viewing and mitigating the creation of microscopic air bubbles in the plurality of syringes 34 or the catheter 26. Such a feature is possible because the stand 102 depicted in FIGS. 12 and 13 positions the plurality of syringes 34 such that the syringes 34 face the stand 102. Alternatively, as depicted in FIG. 14, the stand 102 may position and hold the device 10 in a horizontal direction. Such an example provides the most stable solution because the center of mass of the device 10 is lowest. Additionally, the stand 102 may position and hold the device 10 in a flat, horizontal direction, which does not require the UI to rotate and provides a stable platform to place the device 10 on a surface such as a table.

Moreover, the device 10 may include a stand 102 attached to the housing 30. For example, the housing 30 could include feet that extend from the housing 30 and are fixed in position. In another example, the housing 30 could include a hanger 104 and kickstand 108 incorporated into the housing 30. In such an example, the hanger 104 could be disposed at the distal end of the housing 30 and the kickstand 108 could be disposed toward the proximal end of the housing 30. Both the hanger 104 and the kickstand 108 include a first position, wherein the hanger 104 and the kickstand 108 are stowed, flush with the housing 30, and a second position, wherein the hanger 104 and the kickstand 108 are rotated outwardly from the housing 30. Further, a Velcro strap may be included in such an example to secure the device 10 to the handrail, pole, railing, etc. to which the device 10 is mounted.

Figure 17:
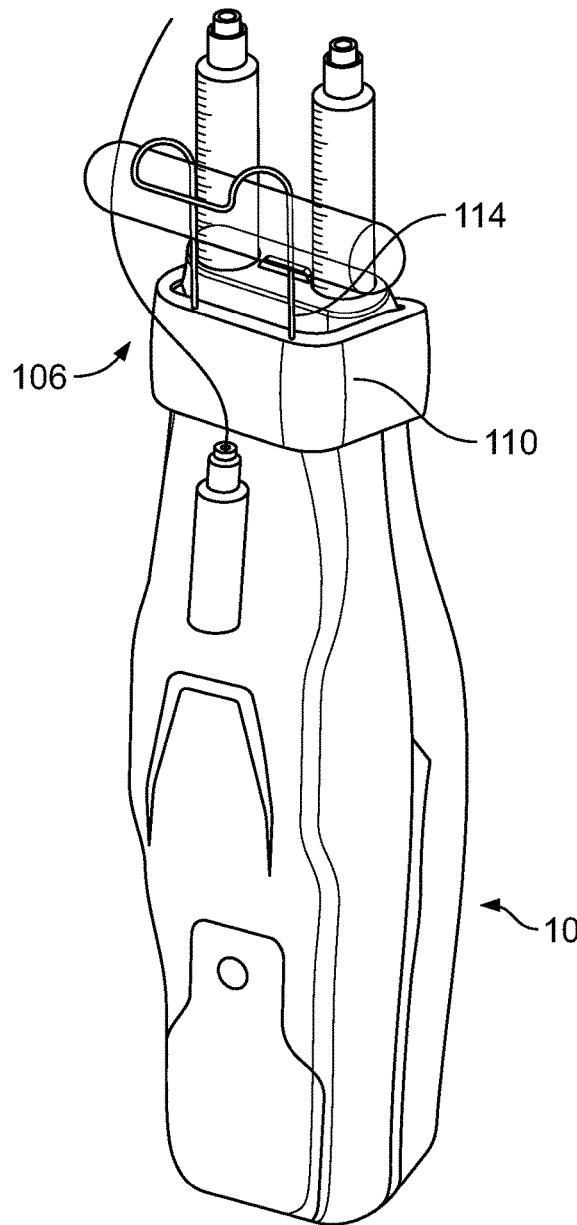
FIG. 17 is a perspective view of the auto-injection device of FIG. 2, but including an example mounting device.
Figure 18:
FIG. 18 is another perspective view of the auto-injection device of FIG. 15.
Figure 19:
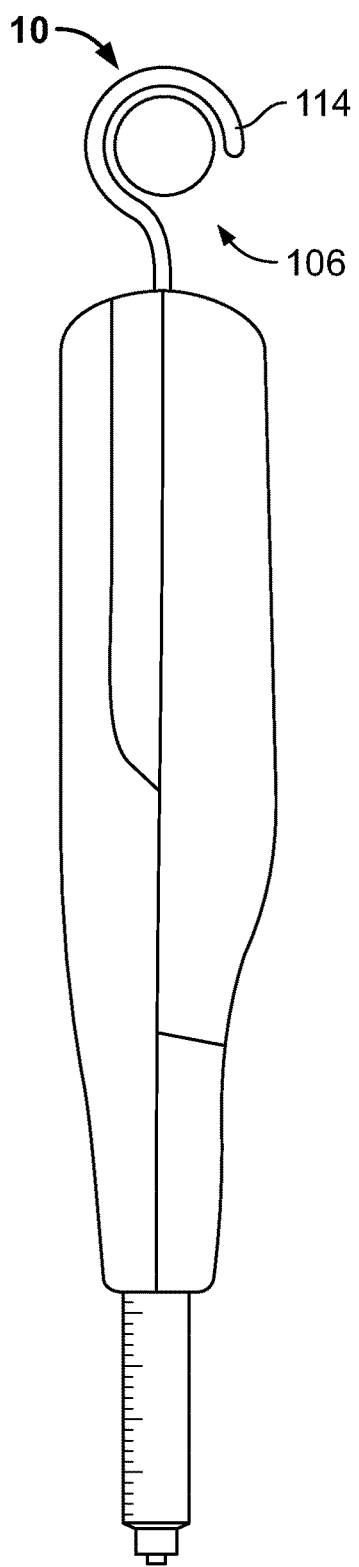
FIG. 19 is a side view of the auto-injection device of FIG. 2, but including another example of a mounting device.
Figure 20:
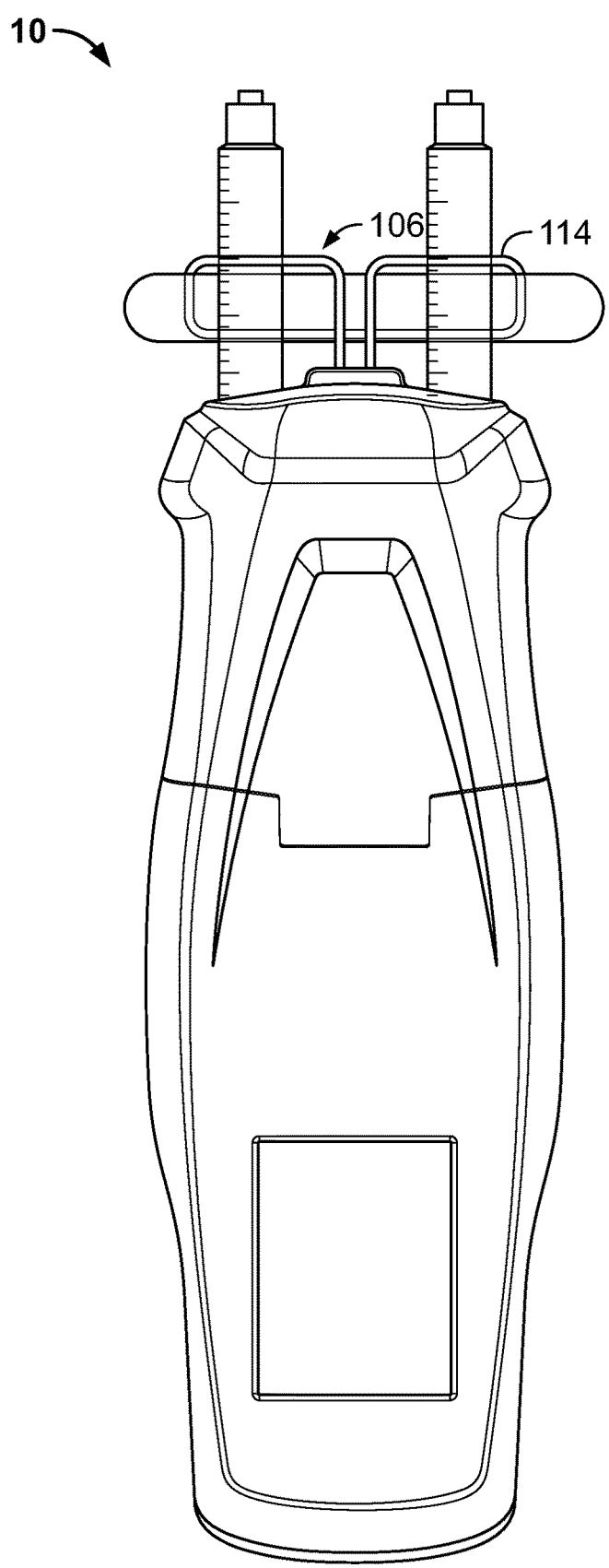
FIG. 20 is a top view of the auto-injection device of FIG. 17.
Figure 21:
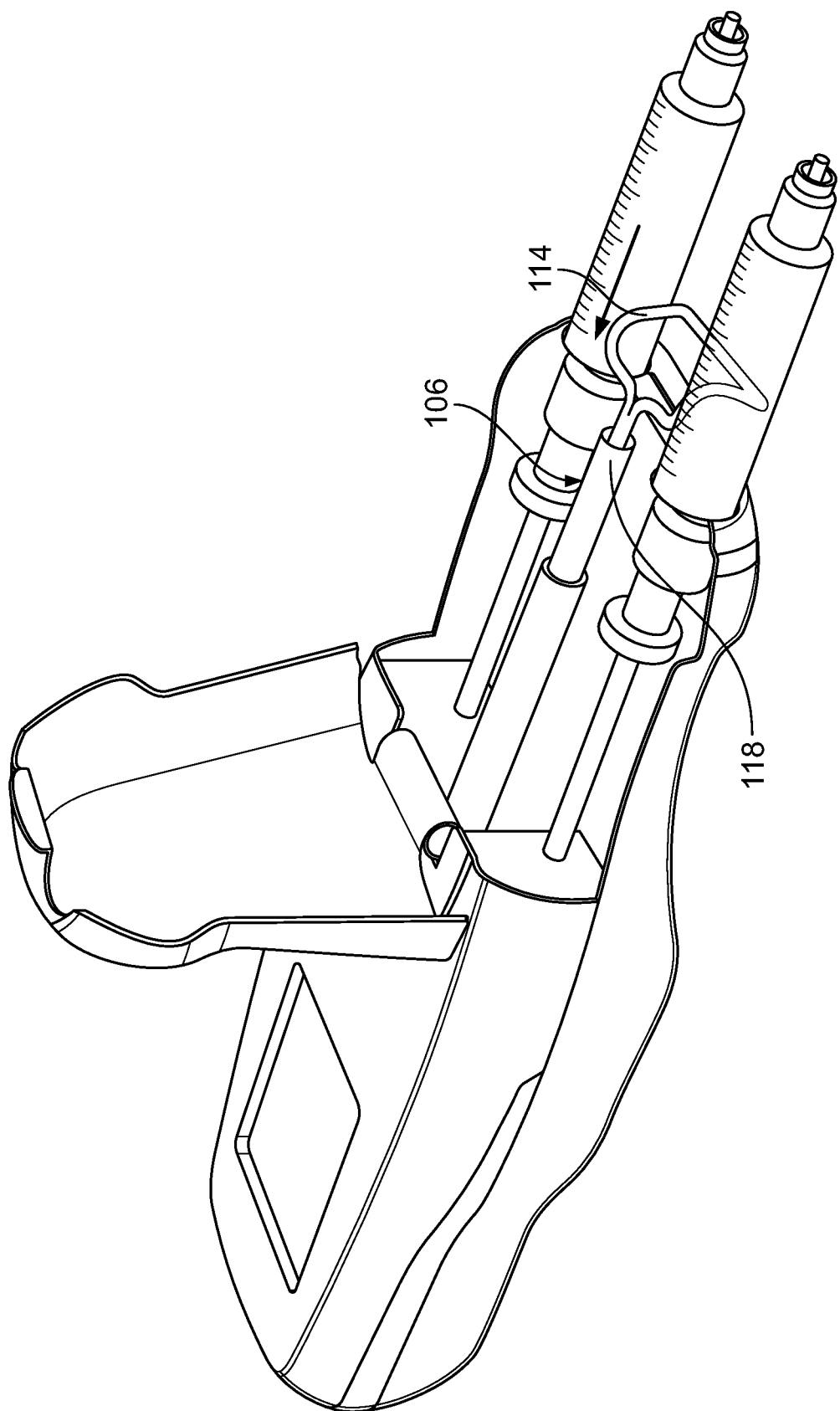
FIG. 21 is a perspective view of the auto-injection device of FIG. 17, but with a portion of the housing in an open position.

The device 10 may, alternatively or additionally, include a mount 106 that allows the device 10 to be hooked onto a handrail, a pole, a railing, or other object. The mount 106 depicted in FIGS. 15 and 16 could be releasably attached to the housing 30 of the device 10. The mount 106 in FIGS. 15 and 16 includes a holder 110 that is releasably securable to the housing 30 and a wired hook 114 that is carried by the holder 110. In some examples the wired hook 114 may be malleable, allowing the wired hook 114 to take on the shape of the object from which the device 10 is to be hung. In other examples, the wired hook 114 may be rigid. While not depicted in FIGS. 15 and 16, the device 10 may further include a Velcro strap to secure the device 10 to the handrail, the pole, the railing, etc. to which the device 10 is mounted. FIGS. 17-19 depict another example of a mount 106 that is carried by the device 10 within the housing 30. In such an example, the mount 106 includes a shaft 118 and a wired hook 114. The shaft 118 is extendable between a first position, wherein the wired hook 114 is disposed within the housing 30, and a second position, wherein the wired hook 114 is disposed outside of the housing 30 for attachment to the handrail, the pole, the railing, or other object. The shaft 118 may, in turn, be locked in the first position or in the second position to securely mount the device 10 to the desired object. A portion of the housing 30 is openable to remove or stow the shaft 118 and the wired hook 114 as depicted in FIG. 19. While not depicted in FIGS. 17-19, the device 10 may further include a Velcro strap to secure the device 10 to the handrail, the pole, the railing, etc. to which the device 10 is mounted.

FIGS. 1-9 will now be referenced to discuss, in greater detail, the operation of the auto-injection device 10. In operation, the device 10 is positioned proximate the infusion and aspiration location 14 (and more particularly the at least one catheter 26). Once in place, the plurality of syringes 34 are fluidly connected to the at least one catheter 26 such that the plurality of syringes 34 are fluidly coupled to the infusion and aspiration location 14 within the patient 18. So positioned, the therapy specific, pre-programmed device 10 may be activated to provide the pre-programmed infusion and/or aspiration.

To activate the device 10, the clinician 22 may, for example, select the pre-programmed infusion and aspiration profile (or the desired infusion and aspiration profile if the device 10 is pre-programmed with multiple profiles) using the display 38. Once the display 38 receives this input, the controller 82 retrieves the selected infusion and aspiration profile from the memory 90. As discussed above, the selected infusion and aspiration profile will include an infusion and aspiration protocol in the form of the computing logic 92, which includes various infusion and aspiration routines, embodied as computer-readable instructions.

Once the controller 82 receives or retrieves the infusion and aspiration profile, the processor 86 carries out the infusion and aspiration protocol stored as computing logic 92 by executing the computer-readable instructions. For example, the infusion and aspiration protocol may include instructions for the processor 86 to actuate one or both drivers 62 and infuse the fluid 24a into the infusion and aspiration location 14. In such an example, the instructions can include instructions to expel the fluid 24a from one or both of the syringes 34. Responsive to these instructions, the driver(s) 62 linearly translate(s) the shaft(s) 58, causing the plunger rod(s) 46 to move from the first position to the second position. Movement of the plunger rod(s) 46 from the first position to the second position expels the fluid 24a from the barrel(s) 42 and into the infusion and aspiration location 14. Such instructions may be used, for example, when a first drug is disposed in a first syringe 34 and a second drug to be used in combination with the first drug is disposed in a second syringe 34. In another example, the infusion and aspiration protocol may include instructions for the processor 86 to actuate one of the drivers 62 and aspirate the fluid 24b from the infusion and aspiration location 14 into one of the barrels 42 and, once the fluid 24b is aspirated from the infusion and aspiration location 14 into the barrel 42, infuse the fluid 24a stored within the other barrel 42 into the infusion and aspiration location 14. To this end, the first driver 62 linearly translates a first shaft 58, causing a first plunger rod 46 to move from the second position to the first position, which draws the fluid 24b from the infusion and aspiration location 14 into the corresponding barrel 42. Once the aspiration is complete, the second driver 62 linearly translates a second shaft 58 causing a second plunger rod 46 to move from the first position to the second position, which expels the fluid 24a from the corresponding barrel 42 and into the infusion and aspiration location 14.

In yet another example, the infusion and aspiration protocol may include instructions for the processor 86 to actuate the first driver 62 to infuse a first fluid 24a in the form of an imaging agent from a first barrel 42 into the infusion and aspiration location 14 and, once the imaging agent is infused or is being infused into the infusion and aspiration location 14, infuse a second fluid 24a from a second barrel 42 into the infusion and aspiration location 14. To this end, the first driver 62 linearly translates the first shaft 58, causing the first plunger rod 46 to move from the first position to the second position, expelling the imaging agent from the barrel 42 of the first syringe 34 into the infusion and aspiration location 14. Once the first plunger rod 46 is in the second position, the second driver 62 actuates the second shaft 58, causing the second plunger rod 46 to move from the first position to the second position, thereby expelling the second fluid 24a from the barrel 42 of the second syringe 34 into the infusion and aspiration location 14. In such an example, the imaging agent can be infused for various purposes. For example, the imaging agent can be infused to confirm placement of the device 10 before infusion of the second fluid 24a. The imaging agent may also be infused to confirm leak pathways in the tissue or tumor prior to infusion of the second fluid 24a. The imaging agent may also be infused in intervals during the infusion of the fluid 24a. In particular, a volume less than a total volume of the imaging agent may be infused prior to infusion of the second fluid 24a and as the second fluid 24a is infused, the imaging agent may be infused on specified intervals for a specified volume. This incremental and regimented infusion of the imaging agent allows the clinician 22 to monitor the infusion of the second fluid 24a in real time.

In another example, the infusion and aspiration protocol may include instructions for the processor 86 to actuate the first and second drivers 62 to simultaneously infuse the fluid 24a into the infusion and aspiration location 14 from the first barrel 42 and aspirate the fluid 24b from the infusion and aspiration location 14 into the second barrel 42. To this end, the first driver 62 linearly translates the first shaft 58, causing the first plunger rod 46 of the first syringe 34 to move from the first position to the second position, thereby expelling the fluid 24a from the barrel 42 of the first syringe 34 into the infusion and aspiration location 14. Simultaneously, the second driver 62 linearly translates the second shaft 58, causing the second plunger rod 46 of the second syringe 34 to move from the second position to the first position, thereby drawing the fluid 24b from the infusion and aspiration location 14 and into the barrel 42 of the second syringe 34. In such an example, the first and second drivers 62 can translate the first and second shafts 58 at the same rate (i.e., expelling and drawing in fluid at a constant flow rate). In other examples, however, the first driver 62 can translate at a first rate and the second driver 62 can translate at a second rate different from the first rate.

In yet another example, the infusion and aspiration protocol can include instructions for the processor 86 to actuate the first and/or second drivers 62 to infuse and/or aspirate the fluid 24a, 24b in connection with the at least one physiological parameter and/or the at least one pressure. In other words, the controller 82 operates the actuators 54 to control the infusion and/or aspiration of the syringes 34 using not only the infusion and aspiration protocol but also one or both of the at least one physiological parameter and at least one pressure.

In particular, in one example, the at least one sensor 94 disposed within the housing 30 measures at least one pressure and transmits the measured at least one pressure to the controller 82. The controller 82 then compares the measured at least one pressure to a stored, threshold pressure and determines if the measured pressure is greater, less than, or equal to the stored, threshold pressure. If the controller 82 determines that the measured pressure is greater than the stored, threshold pressure, the controller 82 transmits a stop signal to the processor 86, which causes the processor 86 to stop the first and/or second drivers 62 from translating the first and/or second shafts 58, which in turn stops the fluid flow to and/or from the device 10.

In another example, at least one sensor disposed within the infusion and aspiration location 14 measures the at least one physiological parameter associated with the patient 18 and transmits the measured at least one physiological parameter to the controller 82. In some cases, the controller 82 may then compare the measured at least one physiological parameter to a stored, threshold physiological parameter and determines if the measured at least one physiological parameter is greater than, less than, or equal to the stored, threshold physiological parameter. If the controller 82 determines that the measured at least one physiological parameter is greater than the stored, threshold physiological parameter, then the controller 82 transmits a stop signal to the processor 86, which causes the processor 86 to stop the first and/or second drivers 62 from translating the first and/or second shafts 58, which stops the fluid flow to and/or from the device 10.

In other examples, however, if the controller 82 determines that the measured parameter(s) (e.g., the measured at least one pressure, the measured at least one physiological parameter, or both) is (are) greater than or less than one or more stored, threshold parameter(s), then the controller 82 transmits a signal to the actuators 54 to compensate for the difference between the measured parameter(s) and the stored, threshold parameter(s). As an example, the controller 82 can transmit a signal to the first actuator 54 to increase the speed at which the first shaft 58 is linearly translating if the measured at least one pressure is less than the stored, threshold pressure. Additionally, the controller 82 can transmit a signal to the second actuator 54 to decrease the speed at which the second shaft 58 is linearly translating if the measured pressure is greater than the stored, threshold pressure.

It will be appreciated that the system described herein may be used in a variety of contexts. For example, the disclosure provides a method of treating Huntington's disease, Spinal Muscular Atrophy (SMA), survival motor neuron (SMN) deficiency, pain, amyotrophic lateral sclerosis (ALS) (including superoxide dismutase 1 (SOD1)-related ALS), multiple sclerosis (e.g., primary progressive multiple sclerosis), Angelman's syndrome, Dravet syndrome, Alzheimer's disease and other tau protein-related disorders, progressive supranuclear palsy (PSP), frontotemporal dementia (FTD), epilepsy, epilepsy pre-visualase, migrane, acute disseminated encephalomyelitis, acute repetitive seizures, meningitis (e.g., neoplastic meningitis), alpha-synuclei-related disorders including Parkinson's Disease, cancer (e.g., central nervous system lymphoma, leptomeningeal cancer, or secondary malignant neoplasms (SMN),), inflammation, Sanfilippo A or B, Friedreich's Ataxia, hereditary cerebral hemorrhage with amyloidosis-Dutch type (HCHWA-D), cerebral amyloid angiopathy (CAA), or amyloid congophilic angiopathy (ACA) using the system described herein to deliver a therapeutic to a desired anatomical site (e.g., the intrathecal space).

Those skilled in the art will recognize that a wide variety of modifications, alterations, and combinations can be made with respect to the above described examples without departing from the scope of the disclosure, and that such modifications, alterations, and combinations are to be viewed as being within the ambit of the inventive concept.

We claim:

1. A therapy specific, pre-programmed, hand-held auto-injection device for delivering a drug to a patient, comprising:
    a housing,
    a plurality of syringes carried by the housing and adapted to be fluidly coupled to an infusion and aspiration location in the patient, each syringe including a barrel partially disposed within the housing, a plunger rod movably disposed within the barrel, a stopper disposed at a proximal end of the plunger rod and disposed within the barrel, and an outlet disposed at a proximal end of the barrel, wherein at least one of the plurality of syringes comprises a fluid;
    at least one actuator disposed within the housing, the at least one actuator having a plurality of shafts coupled to a distal end of a respective plunger rod such that the actuator controls a position of each plunger rod between a first position, in which each stopper is spaced from a proximal end of a respective barrel, and a second position, in which each stopper sealingly engages the proximal end of a respective barrel; and
    a controller disposed within the housing and communicatively coupled to the at least one actuator, the controller configured to retrieve an infusion and aspiration profile from a memory of the controller, the infusion and aspiration profile comprising an infusion and aspiration protocol for at least one of the plurality of syringes, the controller configured to operate the at least one actuator based on the infusion and aspiration protocol, thereby moving the plurality of shafts and changing the position of the plurality of plunger rods,
    wherein movement of the plunger rods from the first position to the second position expels the fluid from a respective barrel, via a respective outlet, and into the infusion and aspiration location, and wherein movement of the plunger rods from the second position to the first position draws a fluid from the infusion and aspiration location into the respective barrel, via the respective outlet, and
    wherein a first plunger rod of the plurality of plunger rods is movable between the first position and the second position at the same time a second plunger rod of the plurality of plunger rods is movable between the first position and the second position.

2. The therapy specific, pre-programmed, hand-held auto-injection device of claim 1, wherein the infusion and aspiration location comprises an intrathecal location, an intracerebroventricular location, or an intratumoral location.

3. The therapy specific, pre-programmed, hand-held auto-injection device of claim 1, wherein the infusion and aspiration protocol comprises a set of instructions that, when executed by a processor of the controller, causes the controller to move the plunger rods from the first position to the second position, causes the controller to move the plunger rods from the second position to the first position, causes the controller to move the plunger rods from the second position to the first position, and after movement of the plunger rods from the second position to the first position, move the plunger rods from the first position to the second position, or combinations thereof.

4. The therapy specific, pre-programmed, hand-held auto-injection device of claim 1, further comprising at least one sensor disposed in the hand-held device and configured to measure at least one pressure associated with the patient, wherein the controller is configured to operate the at least one actuator based on the infusion and aspiration protocol and the at least one pressure.

5. The therapy specific, pre-programmed, hand-held auto-injection device of claim 4, wherein the at least one pressure comprises one or more of an in-line pressure, an infusion pressure, or an aspiration pressure.

6. The therapy specific, pre-programmed, hand-held auto-injection device of claim 1, further comprising at least one sensor disposed in the infusion and aspiration location and configured to measure at least one physiological parameter for the patient, wherein the controller is configured to operate the at least one actuator based on the infusion and aspiration protocol and the at least one physiological parameter.

7. The therapy specific, pre-programmed, hand-held auto-injection device of claim 6, wherein the at least one physiological parameter comprises one or more of a cerebrospinal fluid pressure, a cerebrospinal flow rate, an intratumoral pressure, a cerebroventricular pressure, a heart rate, a respiration rate, a protein level, or a biomarker.

8. The therapy specific, pre-programmed, hand-held auto-injection device of claim 1, further comprising a display communicatively coupled to the controller, wherein the display is configured to receive an input and wherein the controller is configured to operate the actuator based in part on the infusion and aspiration protocol and the received input.

9. The therapy specific, pre-programmed, hand-held auto-injection device of claim 1, wherein the at least one actuator comprises a first actuator configured to control a position of a first plunger rod of a first syringe, and a second actuator configured to control a position of a second plunger rod of a second syringe, and wherein the controller independently controls the first and second actuators.

10. The therapy specific, pre-programmed, hand-held auto-injection device of claim 1, further comprising a transceiver disposed in the housing and communicatively coupled to the controller, wherein the transceiver is configured to wirelessly receive the infusion and aspiration profile.

11. The therapy specific, pre-programmed, hand-held auto-injection device of claim 1, wherein the at least one actuator further comprises a plurality of drivers coupled to the plurality of shafts, respectively.

12. The therapy specific, pre-programmed, hand-held auto-injection device of claim 1, wherein the plurality of syringes comprises a first syringe and a second syringe, the first syringe comprising a drug and the second syringe comprising an imaging agent, or the first syringe comprising a drug and the second syringe comprising a drug.

13. The therapy specific, pre-programmed, hand-held auto-injection device of claim 1, wherein the fluid comprises a nucleic acid, a protein therapeutic, a cell therapy, a small molecule therapeutic, a viral vector encoding a therapeutic protein, or a combination thereof.

14. The therapy specific, pre-programmed, hand-held auto-injection device of claim 13, wherein the fluid comprises the nucleic acid selected from the group consisting of an antisense oligonucleotide, a ribozyme, an miRNA, an siRNA, and shRNA, or a nucleic acid encoding a clustered regularly interspaced short palindromic repeats (CRISPR) associated protein (Cas) system, or a combination thereof.

15. The therapy specific, pre-programmed, hand-held auto-injection device of claim 13, wherein the fluid comprises an antisense oligonucleotide that targets mRNA encoding Huntington protein (HTT) or an antisense oligonucleotide that targets mRNA encoding survival motor neuron-2 (SMN2).

16. A therapy specific, pre-programmed, hand-held auto-injection device for delivering a drug to a patient, comprising:
a housing,
a plurality of syringes carried by the housing and adapted to be fluidly coupled to an infusion and aspiration location in the patient, each syringe including a barrel partially disposed within the housing, a plunger rod movably disposed within the barrel, a stopper disposed at a proximal end of the plunger rod and disposed within the barrel, and an outlet disposed at a proximal end of the barrel, wherein at least one of the plurality of syringes comprises a fluid;
at least one actuator disposed within the housing, the at least one actuator having a plurality of shafts coupled to a distal end of a respective plunger rod and a plurality of drivers coupled to the plurality of shafts, respectively, such that one of the plurality of drivers controls a position of each plunger rod between a first position, in which each stopper is spaced from a proximal end of a respective barrel, and a second position, in which each stopper sealingly engages the proximal end of a respective barrel;
at least one sensor disposed in the hand-held device and configured to monitor a pressure associated with the patient; and
a controller disposed within the housing and communicatively coupled to the at least one actuator, the controller configured to receive an infusion and aspiration profile, the infusion and aspiration profile comprising an infusion and aspiration protocol for at least one of the plurality of syringes, the controller configured to operate the at least one actuator based in part on the infusion and aspiration protocol and the monitored pressure, thereby moving the plurality of shafts and changing the position of the plurality of plunger rods,
wherein movement of the plunger rods from the first position to the second position expels the fluid from a respective barrel, via a respective outlet, and into the infusion and aspiration location, and wherein movement of the plunger rods from the second position to the first position draws a fluid from the infusion and aspiration location into the respective barrel, via the respective outlet,
wherein a first driver of the plurality of drivers is operable to move a first plunger rod of the plurality of plunger rods between the first position and the second position at the same time a second driver of the plurality of drivers is operable to move a second plunger rod of the plurality of plunger rods between the first position and the second position.

17. The therapy specific, pre-programmed, hand-held auto-injection device of claim 16, wherein the infusion and aspiration location comprises an intrathecal location, an intracerebroventricular location, or an intratumoral location.

18. The therapy specific, pre-programmed, hand-held auto-injection device of claim 16, wherein the infusion and aspiration protocol comprises a set of instructions that, when executed by a processor of a controller, causes the controller to move the plunger rods from the first position to the second position, causes the controller to move the plunger rods from the second position to the first position, causes the controller to move the plunger rods from the second position to the first position, and after movement of the plunger rods from the second position to the first position, move the plunger rods from the first position to the second position, or combinations thereof.

19. The therapy specific, pre-programmed, hand-held auto-injection device of claim 16, wherein the at least one pressure comprises one or more of an in-line pressure, an infusion pressure, or an aspiration pressure.

20. The therapy specific, pre-programmed, hand-held auto-injection device of claim 16, further comprising at least one sensor disposed in the infusion and aspiration location and configured to monitor at least one physiological parameter, wherein the controller is configured to operate the at least one actuator based on the infusion and aspiration protocol and the at least one physiological parameter.

21. The therapy specific, pre-programmed, hand-held auto-injection device of claim 20, wherein the at least one physiological parameter comprises one or more of a cerebrospinal fluid pressure, a cerebrospinal flow rate, an intratumoral pressure, a cerebroventricular pressure, a heart rate, a respiration rate, a protein level, or a biomarker.

22. The therapy specific, pre-programmed, hand-held auto-injection device of claim 16, further comprising a display communicatively coupled to the controller, wherein the display is configured to receive an input and wherein the controller is configured to operate the actuator based in part on the infusion and aspiration protocol, the received input, and the monitored pressure.

23. The therapy specific, pre-programmed, hand-held auto-injection device of claim 16, wherein the at least one actuator comprises a first actuator configured to control a position of a first plunger rod of a first syringe, and a second actuator configured to control a position of a second plunger rod of a second syringe, wherein the controller independently controls the first and second actuators; and wherein the first driver is coupled to a first shaft and the second driver is coupled to a second shaft, respectively.

24. The therapy specific, pre-programmed, hand-held auto-injection device of claim 16, further comprising a transceiver disposed in the housing and communicatively coupled to the controller, wherein the transceiver is configured to wirelessly receive the infusion and aspiration profile.

25. The therapy specific, pre-programmed, hand-held auto-injection device of claim 16, wherein the plurality of syringes comprises a first syringe and a second syringe, the first syringe comprising a drug and the second syringe comprising an imaging agent, or the first syringe comprising a drug and the second syringe comprising a drug.

26. The therapy specific, pre-programmed, hand-held auto-injection device of claim 16, wherein the fluid comprises a nucleic acid, a protein therapeutic, a cell therapy, a small molecule therapeutic, a viral vector encoding a therapeutic protein, or a combination thereof.

27. The therapy specific, pre-programmed, hand-held auto-injection device of claim 26, wherein the fluid comprises the nucleic acid selected from the group consisting of an antisense oligonucleotide, a ribozyme, an miRNA, an siRNA, and shRNA, or a nucleic acid encoding a clustered regularly interspaced short palindromic repeats (CRISPR) associated protein (Cas) system, or a combination thereof.

28. The therapy specific, pre-programmed, hand-held auto-injection device of claim 26, wherein the fluid comprises an antisense oligonucleotide that targets mRNA encoding Huntington protein (HTT) or an antisense oligonucleotide that targets mRNA encoding survival.

29. The therapy specific, pre-programmed, hand-held auto-injection device of claim 16, wherein the plurality of drivers is configured to translate the plurality of shafts, respectively, at a constant rate, by pulsating, or in a stepwise manner.

30. A therapy specific, pre-programmed, hand-held auto-injection device for delivering a drug to a patient, comprising:
a housing,
a plurality of syringes carried by the housing and adapted to be fluidly coupled to an infusion and aspiration location in the patient, each syringe including a barrel partially disposed within the housing, a plunger rod having a distal end disposed within the housing and a proximal end movably disposed within the barrel, a stopper disposed at the proximal end of the plunger rod and disposed within the barrel, and an outlet disposed at a proximal end of the barrel, wherein at least one of the plurality of syringes comprises a fluid;
at least one actuator disposed within the housing, the at least one actuator having a plurality of shafts coupled to a distal end of a respective plunger rod and a plurality of drivers coupled to the plurality of shafts, respectively, such that the plurality of drivers controls a position of each plunger rod between a first position, in which each stopper is spaced from a proximal end of a respective barrel, and a second position, in which each stopper sealingly engages the proximal end of a respective barrel; and
a controller disposed within the housing and communicatively coupled to the at least one actuator, the controller configured to retrieve an infusion and aspiration profile from a memory of the controller, the infusion and aspiration profile comprising an infusion and aspiration protocol for at least one of the plurality of syringes, the controller configured to operate the at least one actuator based on the infusion and aspiration protocol, thereby moving the plurality of shafts and changing the position of the plurality of plunger rods,
wherein movement of the plunger rods from the first position to the second position expels the fluid from a respective barrel, via a respective outlet, and into the infusion and aspiration location, and wherein movement of the plunger rods from the second position to the first position draws a fluid from the infusion and aspiration location into the respective barrel, via the respective outlet, and
wherein a first driver of the plurality of drivers is operable to move a first plunger rod of the plurality of plunger rods between the first position and the second position at the same time a second driver of the plurality of drivers is operable to move a second plunger rod of the plurality of plunger rods between the first position and the second position.

* * * * *

UNITED STATES PATENT AND TRADEMARK OFFICE
CERTIFICATE OF CORRECTION

PATENT NO. : 10,675,438 B2  
APPLICATION NO. : 16/191275  
DATED : June 9, 2020  
INVENTOR(S) : PJ Anand et al.

Page 1 of 1

It is certified that error appears in the above-identified patent and that said Letters Patent is hereby corrected as shown below:

On the Title Page

At item (57), Line 15, "respectively barrel" should be -- respective barrel --.

In the Claims

At Column 17, Line 65, Claim 1, "a housing," should be -- a housing; --.

At Column 19, Line 57, Claim 15, "Huntington protein (HTT)" should be -- Huntingtin protein (HTT) --.

At Column 19, Line 63, Claim 16, "a housing," should be -- a housing; --.

At Column 21, Line 52, Claim 28, "Huntington protein (HTT)" should be -- Huntingtin protein (HTT) --.

At Column 22, Line 7, Claim 30, "a housing," should be -- a housing; --.

Signed and Sealed this  
Twenty-sixth Day of January, 2021

Drew Hirshfeld  
*Performing the Functions and Duties of the*  
*Under Secretary of Commerce for Intellectual Property and*  
*Director of the United States Patent and Trademark Office*